(12) United States Patent
Eichele et al.

(10) Patent No.: US 9,770,444 B2
(45) Date of Patent: *Sep. 26, 2017

(54) COMPOSITIONS AND METHODS FOR MODULATING CIRCADIAN SYNCHRONIZATION

(71) Applicant: Max-Planck-Gesellschaft-zur-Förderung der Wissenschaften e.V., München (DE)

(72) Inventors: Gregor Eichele, Göttingen (DE); Henrik Oster, Göttingen (DE); Silke Kiessling, Lincoln, NE (US)

(73) Assignee: MAX-PLANCK-GESELLSCHAFT-ZUR-FÖRDERUNG DER WISSENSCHAFTEN E.V, München (DE)

( * ) Notice: Subject to any disclaimer, the term of this patent is extended or adjusted under 35 U.S.C. 154(b) by 16 days.

This patent is subject to a terminal disclaimer.

(21) Appl. No.: 14/573,638

(22) Filed: Dec. 17, 2014

(65) Prior Publication Data

US 2015/0105428 A1  Apr. 16, 2015

Related U.S. Application Data

(63) Continuation of application No. 13/413,907, filed on Mar. 7, 2012, now Pat. No. 8,946,263.

(60) Provisional application No. 61/451,671, filed on Mar. 11, 2011.

(30) Foreign Application Priority Data

Mar. 10, 2011 (CA) .................................... 2733956

(51) Int. Cl.
*A61K 31/44* (2006.01)
*A61K 31/444* (2006.01)
*A61K 31/7105* (2006.01)
*A61K 31/713* (2006.01)

(52) U.S. Cl.
CPC .......... *A61K 31/444* (2013.01); *A61K 31/713* (2013.01); *A61K 31/7105* (2013.01)

(58) Field of Classification Search
CPC . A61K 31/444; A61K 31/7105; A61K 31/713
USPC ........................................................ 514/332
See application file for complete search history.

(56) References Cited

U.S. PATENT DOCUMENTS 7,973,043 B2    7/2011  Migaly
8,946,263 B2 *  2/2015  Eichele ................ A61K 31/444
                                                          514/332
2007/0270393 A1  11/2007  Buckley et al.

OTHER PUBLICATIONS

Kiessling, Silke et al. "Adrenal glucocorticoids have a key role in circadian resynchronization in a mouse model of jet lag." The Journal of Clinical Investigation. vol. 120, No. 7, Jul. 2010. pp. 2600-2609.

* cited by examiner

*Primary Examiner* — Jennifer M Kim
(74) *Attorney, Agent, or Firm* — DT Ward, PC; Donna T. Ward; Anna E. Stanford

(57) ABSTRACT

The present invention relates to a modulator of glucocorticoid biosynthesis, degradation and/or receptor activation for use in preventing or treating symptoms and/or diseases associated with jet lag. The compositions of the invention may be used as a lead compound for developing a drug for preventing or treating symptoms and/or diseases associated with jet lag. The invention relates to the discovery that administration of the modulator(s) to a subject results in a directional change of the time point of maximum amounts of glucocorticoids in the subject as compared to the time point of maximum amounts of glucocorticoids in a subject not treated with the modulator(s).

9 Claims, 7 Drawing Sheets

COMPOSITIONS AND METHODS FOR MODULATING CIRCADIAN SYNCHRONIZATION

CROSS REFERENCE TO RELATED APPLICATIONS

This application a continuation of U.S. patent application Ser. No. 13/413,907 filed on Mar. 7, 2012, which claims the benefit under 35 U.S.C. 119(a) of Canadian Application No.: 2,733,956 filed on Mar. 10, 2011 and 35 U.S.C. 119(e) of U.S. Provisional Application Ser. No. 61/451,671, filed Mar. 11, 2011, the entirety of which is incorporated herein by reference.

FIELD OF THE INVENTION

The present invention relates to a modulator of glucocorticoid biosynthesis, degradation, and/or receptor activation for use in preventing or treating conditions (symptoms or diseases) associated with jet lag. The invention provides compositions and methods that produce a directional change of the time point of maximum amounts of glucocorticoids as compared to the time point of maximum amounts of glucocorticoids in a subject not treated with the modulator(s).

BACKGROUND OF THE INVENTION

When travelling across a number of time zones or when working changing shifts such as e.g. night shifts, the body clock becomes out of synchronization with the actual time, as it experiences daylight and darkness contrary to the rhythms to which it has grown accustomed: the body's natural pattern is upset, as the rhythms that dictate times for eating, sleeping, hormone regulation and body temperature variations are no longer synchronized to the environment nor to each other in some cases. To the degree that the body cannot immediately re-align these rhythms, it is jet lagged.

Jet lag is characterized by decreased alertness, night time insomnia, poor overall performance (Tapp and Natelson 1989), impaired cognitive skills (Cho et al. 2001), loss of appetite, depressed mood, reduced psychomotor coordination, and gastrointestinal disturbances (Waterhouse et al. 2007). The severity and extent of these symptoms depend on the direction and speed of travel and the number of time zones crossed (Waterhouse et al. 2007; Arendt et al. 2009; Haimov et al. 1999; Srinivasan et al. 2008).

Research has suggested that individuals exposed to chronic jet lag may experience accelerated malignant growth (Filipski et al. 2004) and temporal lobe atrophy combined with spatial cognitive deficits (Cho et al. 2001). It has been shown that rodents subjected to chronic jet lag suffer from cardiomyopathies (Penev et al. 1998) and hastened death upon aging (Davidson et al. 2006).

Circadian clocks are oscillators driven by interlocked positive and negative transcriptional/translational feedback loops. The circadian transcriptional activators circadian locomotor output cycles kaput (CLOCK) and aryl hydrocarbon receptor nuclear translocator-like (ARNTL; also referred to as BMAL1) turn on period (Per1, Per2, and Per3) and cryptochrome (Cry1 and Cry2) genes. PER and CRY proteins are negative regulators repressing CLOCK/ARNTL-mediated transactivation (Dunlap 1999; Reppert and Weaver 2001; van der Horst et al. 1999).

A second loop involves positive and negative regulation of Arntl expression through RAR-related orphan receptor α (RORα) and nuclear receptor subfamily 1, group D, member 1 (NR1D1; also known as REV-ERBα), respectively (Preitner et al. 2002). The transcription factor D site albumin promoter binding protein (DBP) regulates rhythmic activation of downstream target genes (Ripperger et al. 2000), thereby serving as relay mediating the output of the circadian oscillator. The master pacemaker of the hypothalamic suprachiasmatic nuclei (SCN) and also peripheral oscillators all rhythmically express clock genes (Welsh et al. 2004). The SCN appears to synchronize peripheral oscillators present in, for example, the cerebral cortex (Yan et al. 2000; Abe et al. 2001), the retina (Tosini et al. 1996), the liver (Yamazaki et al. 2000), the kidney (Yoo et al. 2004), and the pancreas (Damiola et al. 2000; Liu et al. 2007; Oishi et al. 2000; Schibler et al. 2003) through hormonal and neuronal pathways (Schibler et al. 2003; Perreau-Lenz et al. 2004). Peripheral clocks translate clock time into physiologically meaningful signals via rhythmic activation of clock-controlled genes (Storch et al. 2002; Panda et al. 2002). The temporal disorganization of the circadian system during jet lag is likely to disrupt overall physiological coordination and, hence, be the cause of most jet lag-associated symptoms (Arendt et al. 2009).

To date, surprisingly little is known about the molecular processes underlying resynchronization of internal and external rhythms during jet lag. Pioneering studies with rodents expressing a period gene-driven luciferase reporter have provided inroads to understanding the underlying mechanism (Yamazaki et al. 2000). It was proposed that overall clock resetting is initiated at the level of the SCN, with rapid reentrainment of period gene rhythms followed by that of cryptochrome genes (Reddy et al. 2002). Reddy and colleagues provide evidence that cryptochrome rhythm entrainment in the SCN closely correlates with that of behaviour (Reddy et al. 2002).

Another aspect of perturbation was shown at the level of SCN morphology, where cells can be separated in ventral and dorsal regions that show different resetting kinetics during the period of desynchrony (Davidson et al. 2009).

Collectively, the results of these studies, which included a limited number of tissues and circadian genes, suggest that coordination of clock gene expression is globally disrupted during jet lag.

At present, common strategies to alleviate jet lag and the syndromes and diseases associated therewith aim at adjusting the body clock to the new time zone prior to travel (Waterhouse et al. 2007). Therefore, most treatments are based on pre-flight plans, including long-term light conditioning, sometimes in combination with timed melatonin administration (Arendt et al. 2009).

Furthermore, it has recently been shown that in hamsters, the phosphodiesterase inhibitor sildenafil enhances circadian responses to light and accelerates reentrainment after phase advances of the LD cycle (Agostino et al. 2007).

However, despite the above described advances in understanding the mechanisms underlying jet lag and in the development of treatments to alleviate the effects of jet lag, no satisfying therapeutic is at present available for the treatment of symptoms and diseases associated with jet lag.

The findings of the present invention not only substantiate the importance of glucocorticoid rhythms in jet lag adaptation, but also provide a novel therapeutic model for the treatment of jet lag and its associated symptoms.

SUMMARY OF THE INVENTION

The present invention comprises modulators of glucocorticoid biosynthesis, degradation, and/or receptor activation for use in preventing or treating conditions (symptoms or diseases) associated with jet lag and methods attendant thereto.

In one embodiment of the invention is a modulator of at least one of glucocorticoid biosynthesis, degradation or receptor activation for use in preventing or treating symptoms and/or diseases associated with jet lag.

The modulator of may be administered to a subject wherein the administration results in a directional change of the time point of maximum amounts of glucocorticoids in the subject as compared to the time point of maximum amounts of glucocorticoids in said subject not treated with the modulator.

In another embodiment, the invention embraces classes of modulators. These include, but are not limited to, small organic molecules, an antibody or a fragment or derivative thereof, an aptamer, an siRNA, an shRNA, an miRNA, a ribozyme, and an antisense nucleic acid molecule.

Diseases and/or symptoms to be treated by the modulators of the present invention include, but are not limited to, sleep disruption, impaired cognitive skills, loss of appetite, depression, reduced psychomotor coordination, gastrointestinal disturbances, decreased alertness, malignant cell growth, temporal lobe atrophy and cardiomyopathies.

In one embodiment, the amplitude of maximum glucocorticoid amounts is not significantly altered upon administration.

In one embodiment, the time point of maximum amounts of glucocorticoids in a subject treated with said modulator is earlier than the time point of maximum amounts of glucocorticoids from a subject not treated with the modulator and wherein this earlier time point results from the administration of the modulator in the first half of the rest phase of the subject to be treated.

In a further embodiment, the time point of maximum amounts of glucocorticoids in a subject treated with the modulator is later than the time point of maximum amounts of glucocorticoids from a subject not treated with the modulator and wherein this later time point results from the administration of the modulator in the first half of the active phase of the subject to be treated.

In one embodiment of the invention, the modulators are administered at least one time prior to and/or at the time of initiating activities that cause jet-lag. They may also be administered once a day.

In one embodiment, the modulator is metyrapone.

DETAILED DESCRIPTION

Figure 1:
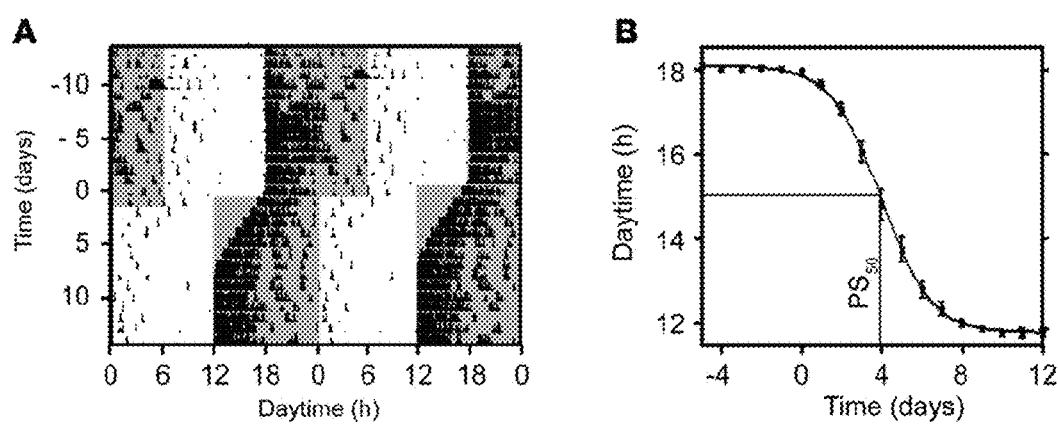
FIG. 1: Behavioral entrainment during jet lag. (A) Representative double-plotted activity recording of a mouse before and after 6-hour LD phase advance applied at day 1. Tick marks represent wheel running activity; gray shading denotes dark lighting conditions. (B) Average onset of mice (n=9) during jet lag. Phase Shift (PS) $PS_{50}$ (4.0±0.1 days) was defined as the time at which half the phase shift was completed. All values are average±SEM.

The present invention relates to a modulator of glucocorticoid biosynthesis, degradation, and/or receptor activation for use in preventing or treating conditions (symptoms or diseases) associated with jet lag. The invention provides compositions and methods that produce a directional change of the time point of maximum amounts of glucocorticoids as compared to the time point of maximum amounts of glucocorticoids in a subject not treated with the modulator(s).

The present invention further relates to a method of preventing or treating symptoms and/or diseases associated with jet lag.

In this specification, a number of documents including patent applications and manufacturer's manuals are cited. The disclosures of these documents are herewith incorporated by reference in their entirety. More specifically, all referenced documents are incorporated by reference to the same extent as if each individual document was specifically and individually indicated to be incorporated by reference.

Accordingly, the present invention relates to a modulator of glucocorticoid biosynthesis and/or a modulator of glucocorticoid degradation and/or a modulator for glucocorticoid receptor activity for use in preventing or treating symptoms and/or diseases associated with jet lag or as a lead compound for developing a drug for preventing or treating symptoms and/or diseases associated with jet lag, wherein administration of the modulator(s) to a subject results in a directional change of the time point of maximum amounts of glucocorticoids in the subject as compared to the time point of maximum amounts of glucocorticoids in a subject not treated with the modulator(s).

The term "glucocorticoid/s", as used in accordance with the present invention, relates to a class of steroid hormones that bind to the glucocorticoid receptor. They play a part in the regulation of a wide range of physiological and pathophysiological processes including, metabolism, immune response, development, cognition and arousal. Activation of the glucocorticoid receptor complex up- or downregulates the expression of many proteins that mediate these processes. Binding of glucocorticoitds to their cognate receptors evokes a translocation of the receptor from the cytosol into the nucleus, enabling the receptor to bind to and activate target genes. Examples of glucocorticoids include, without being limiting, cortisol (also referred to as hydrocortisone) and corticosterone, with cortisol being the most important human glucocorticoid. Various synthetic glucocorticoids are available, such as for example Dexamethasone, Prednisone, Prednisolone, Betamethasone or Triamcinolone.

The term "modulator of glucocorticoid biosynthesis" as used in accordance with the present invention refers to one or more, or a class of, compounds that directly or indirectly interact with one or more of the molecules involved in the synthesis pathway of glucocorticoids and thus alters the amount, levels or expression pattern of glucocorticoids produced. Thus, included in this term are for example compounds that interact with enzymes involved in the various steps of glucocorticoid biosynthesis. The term "modulator", as used herein, refers to one or more, or class of, compounds that alter the biological activity of their target. In one embodiment, the modulator(s) of the present invention are selected from the group consisting of inhibitors and activators. In a further embodiment, the modulator of glucocorticoid biosynthesis is an inhibitor of glucocorticoid biosynthesis.

Biosynthesis of glucocorticoids has been described in the art (see e.g. Doghman et al. 2007) and includes the steps of uptake of cholesterol from lipoproteins and transport into the mitochondrion, cleavage of cholesterol to pregnenolone, conversion to (17a-hydroxy-) progesterone and subsequent hydroxylation to 11-deoxy-cortisol and, in a last step, cortisol. Also included in the term "modulator of glucocorticoid biosynthesis" are compounds that indirectly interact with glucocorticoid biosynthesis by e.g. affecting the gene expression of one or more molecules involved in the control of glucocorticoid biosynthesis such as ACTH and its receptor (MC2R), StaR, SP1, DAX or the LDL receptor (see e.g. Stocco et al. 2005). Table 1 provides an overview over some of the known molecules and enzymes involved in glucocorticoid biosynthesis as well as known modulators thereof.

TABLE 1

Regulators of Adrenal Steriodogenesis.

| Gene | Enzyme function | Entrez ID (mouse) | Entrez ID (human) | EC Number | Inhibitor(s) |
|---|---|---|---|---|---|
| Ldlr | no | 16835 | 3949 | | |
| Scarb2 | no | 12492 | 950 | | |
| Scp2 | no | 20280 | 6342 | | |
| Lipe | yes | 16890 | 3991 | 3.1.1.79 | cyclipostins; isoxazolones |
| Star | no | 20845 | 6770 | | |
| Hspa5 | no | 14828 | 3309 | | |
| Sts | yes | 20905 | 412 | 3.1.6.2 | BN83495, Stx213, Stx64 |
| Stard4/5 | no | 170459, 170460 | 134429, 80765 | | |
| Cyp11a1 | yes | 13070 | 1583 | 1.14.15.6 | aminoglutethimide |

TABLE 1-continued

Regulators of Adrenal Steriodogenesis.

| Gene | Enzyme function | Entrez ID (mouse) | Entrez ID (human) | EC Number | Inhibitor(s) |
|---|---|---|---|---|---|
| Nr3c1 | no | 14815 | 2908 | | |
| Nr0b1 | no | 11614 | 190 | | |
| Hsd3b | yes | 111785 | 3283, 3284 | 1.1.1.145, 5.3.3.1 | cyanoketone, trilostane |
| Cyp21 | yes | 13079 | 1589 | 1.14.99.10, 1.14.99.10 | YZ5ay |
| Por | yes | 18984 | 124015 | 1.6.2.4 | diphenyleneiodonium sulfate |
| Cyp11b1/2 | yes | 110115, 13072 | 1584, 1585 | 1.14.15.4, 1.14.15.5 | FAD286, aryl methyl sulfones, metyrapone, etomidate, FAD |
| Fdxr | yes | 14149 | 2232 | 1.18.1.2 | Zn-ferrocyanide |
| Fdx1 | no | 14148 | 2230 | | |
| Tnf | no | 21926 | 7124 | | |
| Nr2f1 | no | 13865 | 7025 | | |
| Nppa | no | 230899 | 4878 | | |
| Ifngr | no | 15979 | 3459 | | |
| Il1b | no | 16176 | 3553 | | |
| Sik1 | yes | 17691 | 150094 | 2.7.11.1 | |
| Yy1 | no | 22632 | 7528 | | |
| Tgfb | no | 21803, 21808, 21809 | 7040, 7042, 7043 | | |
| Vdac1 | no | 22333 | 7416 | | |
| Slc25a | no | various | various | | |
| Tspo | no | 12257 | 706 | | |
| Dbi | no | 13167 | 1622 | | |
| Pla2 | yes | various | various | 3.1.1.4 | quinacrine, 7,7-dimethyleicosadienoic acid, 4-BPB, mepacrine, LY333013, PLIβ, varespladib, lipocortm |
| Gn | no | various | various | | |
| Prkc | yes | various | various | 2.7.11.13 | AEB071, PKC412, bisindolylmaleimide I, Ro-32-0432, calphostin c, . . . |
| Plcg | yes | 18803, 234779 | 5335, 5336 | 3.1.4.11 | U-73122, PAO, Y766 peptide |
| Camk2 | yes | 12322, 12323 | 815, 816 | 2.7.11.17 | Lavendustin C, CK59, KN-62, KN-93, CaM-KIIN |
| Agt | no | 11606 | 183 | | |
| Agtr2 | no | 11609 | 186 | | |
| Jun | no | 16476 | 3725 | | |
| Nfy | no | 18044, 18045, 18046 | 4800, 4801, 4802 | | |
| Atf1 | no | 11908 | 466 | | |
| Gata4 | no | 14463 | 2626 | | |
| Cebp | no | 12606, 12608 | 1050, 1051 | | |
| Scop | no | 235623 | 22937 | | |
| Crem | no | 12916 | 1390 | | |
| Nr5a1 | no | 26423 | 2516 | | |
| Creb1 | no | 12912 | 1385 | | |
| Sp1 | no | 20683 | 6667 | | |
| Igf1 | no | 16000 | 3479 | | |
| Igfr1 | no | 16001 | 3480 | | |
| Pp1 | yes | various | various | 3.1.3.16 | tautomycetin, calyculin A, |
| Prka | yes | various | various | 2.7.11.11 | 5-24, 5-22, 14-24, fragment (6-22) amide, Rp-cAMPS, H8, H89, H7, . . . |
| Mc2r | no | 17200 | 4158 | | |
| Adcy | yes | various | various | 4.6.1.1 | DC5, 2',5'-Dideoxyadenosine, KH7, NKY80, SQ22536, . . . |
| Adrb | no | 11554, 11555, 11556 | 153, 154, 155 | | |
| Htr5a | no | 15563 | 3361 | | |
| Avpr1a | no | 54140 | 552 | | |

Also encompassed by the term "modulator of glucocorticoid biosynthesis" are compounds that interfere with clock genes, thus resulting in the modulation of glucocorticoid biosynthesis. For example, and without wishing to be bound by theory, it is postulated that in addition to its known function as steroid-11-beta hydroxylase inhibitor, metyrapone might have a further or additional effect such as for example by binding to the heme moiety of the circadian clock proteins RevErbA (Nr1d1) and RevErbB (Nr1d2). Such a binding could affect the known ability of RevErbA and RevErbB to interact with transcriptional corepressor NCoR and thereby affect the expression of the circadian protein Bmall. Because adrenal clock genes have been shown to regulate glucocorticoid production rhythms, a modulation of clock gene/protein activity might translate into changes in glucocorticoid secretion (Oster et al. 2006). Thus, other REV-ERBα/REV-ERBβ agonist such as SR6452 (Kumar et al. 2010) could also affect circadian rhythms in a way similar to what is shown in the examples below. It is known that thousands of genes are clock-controlled and it is therefore conceivable that in particular tissues such clock-controlled genes may include those mediating glucocorticoid biosynthesis and/or degradation The term "modulator of glucocorticoid degradation" as used in accordance with the present invention refers to compounds that interact with one or more of the molecules involved in the degradation of glucocorticoids or that destabilize glucocorticoids and thus alter the amount of glucocorticoids. Preferably, the modulator of glucocorticoid degradation is an activator of glucocorticoid degradation.

Degradation of glucocorticoids has been described in the art (see e.g. Müssig et al. 2010) and occurs via reduction to mono-, di- or tetrahydrocortisol or conversion to cortisone and subsequent reduction to hydrocortisone in the liver or the kidney, followed by excretion via urine or feces.

Preferably, the amount of glucocorticoid is altered by the modulators in accordance with the present invention by at least 10%, more preferred by at least 20%, such as for example at least 30%, more preferably at least 40% and even more preferably at least 50% compared to the amount of glucocorticoid present in the absence of the modulator(s). More preferably the amount of glucocorticoid is altered by at least 60%, such as at least 70%, more preferably at least 80%, such as at least 90%, more preferably at least 95% and most preferably by at least 99% compared to the amount of glucocorticoid present in the absence of the modulator(s). Preferably, the above recited amounts of alterations in glucocorticoid amounts are alterations obtained at a particular time point relative to that same time point on one or more different, e.g. previous days and within the same subject, such as for example at 6 am on two consecutive days. It is further preferred that the maximum amount of glucocorticoid at the peak time (i.e. the amplitude of maximum glucocorticoid amounts) remains the same, i.e. the above defined alteration in glucocorticoid amounts at a time point different from the time point of the glucocorticoid maximum results in a shift of said time point of maximum amounts of glucocorticoid to occur later or earlier than it would do in the absence of the modulator(s).

The efficiency of a modulator can be quantified by comparing the amount of glucocorticoids in the presence of the modulator to the amount of glucocorticoids in the absence of the modulator. For example, the amount of glucocorticoids present prior to and after administration of the modulator may be determined, wherein a reduction in the amount of glucocorticoids after administration of the modulator as compared to prior to said administration is indicative of a successful inhibition of glucocorticoid biosynthesis or successful degradation of glucocorticoids. Means and methods to determine the amount of glucocorticoids in a sample are well known in the art and include, without being limiting, corticoid metabolite extraction and quantification by mass spectrometry (in particular GC-MS), RIA, HPLC or ELISA as described in e.g. Holder et al. 2006. In one embodiment, the sample employed for determining glucocorticoid amounts is selected from the group consisting of saliva, blood, feces and urine.

The term "a modulator of glucocorticoid receptor activation", as used in accordance with the present invention, relates to compounds capable of increasing or reducing the biological activity of glucocorticoid receptors. In one embodiment, the modulator is an activator of glucocorticoid receptor activity. Non-limiting examples of activators of glucocorticoid receptor activation include their naturally occurring ligands, i.e. glucocorticoids as well as synthetically or semi-synthetically produced agonists. Examples of naturally occurring as well as synthetic glucocorticoids have been provided herein above.

Glucocorticoid receptor activation can be determined by the skilled person, e.g. by measuring the activation of the transcriptional targets downstream of the receptor. Such measurements include for example determining the activation of the glucocorticoid response element via for example reporter gene expression as well as measuring alterations in target gene expression, such as for example Egfp, S1c19a2, Gilz1, Per1/2, Adh1, Ddx5, Hsp1β and many others such as recently described by Reddy and coworkers (Reddy et al. 2009). Timed activation of the glucocorticoid receptor in the pituitary or the hypothalamus, via feedback mechanisms, results in a directional change of the time point of maximum activation of the hypothalamus/pituitary/adrenal (hpa) axis via shifting of corticotropin releasing hormone (CRH) or adrenocorticotropin (ACTH) secretion from these tissues. Hpa axis activity, inturn, determines glucocorticoid secretion from the adrenal cortex.

The term "modulator(s)", as used in accordance with the present invention, is understood as referring to either a single modulator as well as to a combination of any of the modulators recited herein. For example, it is envisaged that a combination of an inhibitor of glucocorticoid biosynthesis with an activator of glucocorticoid degradation may be suitable to achieve the desired directional change of the time point of maximum amounts of glucocorticoid more quickly or at lower dosages of the individual modulators as compared to the dosages of the modulator(s) when employed on their own. Thus, any combination of the herein recited modulators is explicitly envisaged, provided that it achieves the intended directional change of the time point of maximum amounts of glucocorticoid levels.

The modulator(s) of the present invention may achieve their modulatory activity via altering the activity or gene expression of a target molecule (e.g. of a molecule of the synthesis or degradation pathway for glucocorticoid or of the glucocorticoid receptor), preferably by performing one or more of the following effects: (i) the protein performs its biochemical function with altered efficiency in the presence of the modulator, (ii) the translation of the mRNA encoding the protein to be affected is altered, and (iii) the transcription of the gene encoding the protein to be affected is altered.

For example, where the target molecule is a positive regulator of glucocorticoid biosynthesis, then it would be desired to reduce the biochemical efficiency or the translation or transcription of said target molecule in order to achieve an inhibition of glucocorticoid biosynthesis. In order to increase glucocorticoid biosynthesis, it would be desired to increase the biochemical efficiency or the translation or transcription of said target molecule. Where the target molecule is, on the other hand, a negative regulator of glucocorticoid biosynthesis, the alteration in the efficiency or the translation or transcription of said target molecule preferably is an increase in order to achieve reduced glucocorticoid levels or a decrease in order to achieve increased glucocorticoid levels. Similarly, where the target molecule enhances glucocorticoid degradation, then an increase in the efficiency or the translation or transcription of said target molecule is desired in order to achieve reduced glucocorticoid levels while a decrease is desired in order to achieve increased glucocorticoid levels. Where the target molecule instead is a negative regulator of glucocorticoid degradation, an increase in the efficiency or the translation or transcription of said target molecule is desired in order to achieve increased glucocorticoid levels while a decrease is desired in order to achieve reduced glucocorticoid levels.

Compounds falling in class (i) interfere with molecular functions of the protein to be modulated, in the present case for example with the transport or the conversion of glucocorticoid precursors in the adrenal. Accordingly, active site binding compounds, in particular compounds capable of binding to steroid transporters or cytochrome p450 enzymes are envisaged herein. Antibodies specifically binding to and interacting with the molecular functions of the target protein also fall into class (i). Class (ii) comprises antisense constructs and constructs for performing RNA interference (e.g. siRNA, shRNA, miRNA) well known in the art (see, e.g. Zamore (2001) Nat. Struct. Biol. 8(9), 746; Tuschl (2001) Chembiochem. 2(4), 239). Compounds of class (iii) include compounds interfering with the transcriptional machinery and/or its interaction with the promoter of said genes and/or with expression control elements remote from the promoter such as enhancers. It will be appreciated by the skilled person that also class (ii) and (iii) compounds might act as modulators of glucocorticoid degradation, for example when interfering with mRNA transcription or translation of target molecules that serve to maintain glucocorticoid levels, thereby reducing the amount of said molecule and consequently resulting in a degradation of glucocorticoid.

The function of any of the modulators referred to in the present invention may be identified and/or verified by using high throughput screening assays (HTS). High-throughput assays, independently of being biochemical, cellular or other assays, generally may be performed in wells of microtiter plates, wherein each plate may contain, for example 96, 384 or 1536 wells. Handling of the plates, including incubation at temperatures other than ambient temperature, and bringing into contact of test compounds with the assay mixture is preferably affected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to the observed biological activity.

The determination of binding of potential modulators can be effected in, for example, any binding assay, preferably biophysical binding assay, which may be used to identify binding test molecules prior to performing a functional/activity assay with the modulator(s). Suitable biophysical binding assays are known in the art and comprise fluorescence polarisation (FP) assay, fluorescence resonance energy transfer (FRET) assay and surface plasmon resonance (SPR) assay. For example, a modulator acting via binding to an enzyme involved in the biosynthesis of glucocorticoids, and thereby modulating the activity of said enzyme, may be tested by FRET by labelling either the modulator or the enzyme with a donor chromophore and the other molecule with an acceptor chromophore. These chromophore-labelled molecules are then mixed with each other. When they are dissociated, donor emission can be detected upon donor excitation at the appropriate wavelength. However, when the donor and acceptor are in proximity (1-10 nm) due to the interaction of the modulator with the enzyme, the acceptor emission is predominantly observed because of the intermolecular FRET from the donor to the acceptor.

In cases where the modulator acts by affecting the expression level of a target protein, the determination of the expression level of the protein can, for example, be carried out on the nucleic acid level or on the amino acid level.

Methods for determining the expression of a protein on the nucleic acid level include, but are not limited to, Northern blotting, PCR, RT-PCR or real-time RT-PCR. PCR is well known in the art and is employed to make large numbers of copies of a target sequence. This is done on an automated cycler device, which can heat and cool containers with the reaction mixture in a very short time. The PCR, generally, consists of many repetitions of a cycle which consists of: (a) a denaturing step, which melts both strands of a DNA molecule and preferably terminates all previous enzymatic reactions; (b) an annealing step, which is aimed at allowing the primers to anneal specifically to the melted strands of the DNA molecule; and (c) an extension step, which elongates the annealed primers by using the information provided by the template strand. Generally, PCR can be performed, for example, in a 50 µl reaction mixture containing 5 µl of 10×PCR buffer with 1.5 mM $MgCl_2$, 200 µM of each deoxynucleotide triphosphate, 0.5 µl of each primer (10 µM), about 10 to 100 ng of template DNA and 1 to 2.5 units of Taq Polymerase. The primers for the amplification may be labeled or be unlabeled. DNA amplification can be performed, e.g., with a model 2400 thermal cycler (Applied Biosystems, Foster City, Calif.): 2 min at 94° C., followed by 30 to 40 cycles consisting of annealing (e.g. 30 s at 50° C.), extension (e.g. 1 min at 72° C., depending on the length of DNA template and the enzyme used), denaturing (e.g. 10 s at 94° C.) and a final annealing step at 55° C. for 1 min as well as a final extension step at 72° C. for 5 min. Suitable polymerases for use with a DNA template include, for example, *E. coli* DNA polymerase I or its Klenow fragment, T4 DNA polymerase, Tth polymerase, Taq polymerase, a heat-stable DNA polymerase isolated from *Thermus aquaticus*, Vent, Amplitaq, Pfu and KOD, some of which may exhibit proof-reading function and/or different temperature optima. However, it is well known in the art how to optimize PCR conditions for the amplification of specific nucleic acid molecules with primers of different length and/or composition or to scale down or increase the volume of the reaction mix. The "reverse transcriptase polymerase chain reaction" (RT-PCR) is used when the nucleic acid to be amplified consists of RNA. The term "reverse transcriptase" refers to an enzyme that catalyzes the polymerization of deoxyribonucleotide triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. High-temperature RT provides greater primer specificity and improved efficiency. U.S. patent application Ser. No. 07/746, 121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT Reaction can be performed, for example, in a 20 μl reaction mix containing: 4 μl of 5×AMV-RT buffer, 2 μl of Oligo dT (100 μg/ml), 2 μl of 10 mM dNTPs, 1 μl total RNA, 10 Units of AMV reverse transcriptase, and H$_2$O to 20 μl final volume. The reaction may be, for example, performed by using the following conditions: The reaction is held at 70° C. for 15 minutes to allow for reverse transcription. The reaction temperature is then raised to 95° C. for 1 minute to denature the RNA-cDNA duplex. Next, the reaction temperature undergoes two cycles of 95° C. for 15 seconds and 60° C. for 20 seconds followed by 38 cycles of 90° C. for 15 seconds and 60 C.° for 20 seconds. Finally, the reaction temperature is held at 60° C. for 4 minutes for the final extension step, cooled to 15° C., and held at that temperature until further processing of the amplified sample. Any of the above mentioned reaction conditions may be scaled up according to the needs of the particular case. The resulting products are loaded onto an agarose gel and band intensities are compared after staining the nucleic acid molecules with an intercalating dye such as ethidium bromide or SybrGreen. A lower band intensity of the sample treated with the compound as compared to a non-treated sample indicates that the compound successfully inhibits the expression of the protein on the nucleic acid level while a higher band intensity of the sample treated with the compound as compared to a non-treated sample indicates that the compound successfully activates the expression of the protein on the nucleic acid level.

Real-time PCR employs a specific probe, in the art also referred to as TaqMan probe, which has a reporter dye covalently attached at the 5' end and a quencher at the 3' end. After the TaqMan probe has been hybridized in the annealing step of the PCR reaction to the complementary site of the polynucleotide being amplified, the 5' fluorophore is cleaved by the 5' nuclease activity of Taq polymerase in the extension phase of the PCR reaction. This enhances the fluorescence of the 5' donor, which was formerly quenched due to the close proximity to the 3' acceptor in the TaqMan probe sequence. Thereby, the process of amplification can be monitored directly and in real time, which permits a significantly more precise determination of expression levels than conventional end-point PCR. Also of use in Real time RT-PCR experiments is a DNA intercalating dye such as SybrGreen for monitoring the de novo synthesis of double stranded DNA molecules. The resulting products are simultaneously quantified by plotting fluorescence against cycle number on a logarithmic scale. A threshold for detection of fluorescence above background is determined. The cycle at which the fluorescence from a sample crosses the threshold is called the cycle threshold, $C_t$. The quantity of DNA theoretically doubles every cycle during the exponential phase and relative amounts of DNA can be calculated, e.g. a sample whose $C_t$ is 3 cycles earlier than another's has $2^3=8$ times more template. Thus, an earlier $C_t$ of a sample treated with the compound of interest as compared to a non-treated sample indicates that the compound successfully activates the expression of the protein on the nucleic acid level while a later $C_t$ of a sample treated with the compound of interest as compared to a non-treated sample indicates that the compound successfully inhibits the expression of the protein on the nucleic acid level.

Methods for the determination of the expression of a protein on the amino acid level include but are not limited to western blotting or polyacrylamide gel electrophoresis in conjunction with protein staining techniques such as Coomassie Brilliant blue or silver-staining. The total protein is loaded onto a polyacrylamide gel and electrophoresed. Afterwards, the separated proteins are transferred onto a membrane, e.g. a polyvinyldifluoride (PVDF) membrane, by applying an electrical current. The proteins on the membrane are exposed to an antibody specifically recognising the protein of interest. After washing, a second antibody specifically recognising the first antibody and carrying a readout system such as a fluorescent dye is applied. The amount of the protein of interest is determined by comparing the fluorescence intensity of the protein derived from the sample treated with the compound of interest and the protein derived from a non-treated sample. A lower fluorescence intensity of the protein derived from the sample treated with the compound indicates a successful inhibitor of the protein while a higher fluorescence intensity of the protein derived from the sample treated with the compound indicates a successful activator of the protein. Also of use in protein quantification is the Agilent Bioanalyzer technique.

In accordance with the present invention, the following developments are considered for further optimisation of the modulator(s), in particular where the modulator(s) are used as a lead compound for the development of a drug for preventing or treating symptoms and/or diseases associated with jet lag: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/ exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff s bases, oximes, acetales, ketales, enolesters, oxazolidines, thiazolidines or combinations thereof. The term "a lead compound" in accordance with the present invention refers to a compound which can be further optimised, in particular to be e.g. pharmaceutically more acceptable and/or to have an altered pharmacokinetic behaviour useful to treat the above mentioned symptoms and/or diseases.

The various steps recited above are generally known in the art. They include or rely on quantitative structure-activity relationship (QSAR) analyses (Kubinyi (1992) "Hausch-Analysis and Related Approaches", VCH Verlag, Weinheim), combinatorial biochemistry, classical chemistry and others (see, for example, Holzgrabe and Bechtold (2000) Deutsche Apotheker Zeitung 140(8), 813).

The term "jet lag" in accordance with the present invention relates to a physiological condition which ensues when the internal circadian rhythms and the external time are out of synchrony, which is medically also referred to as "desynchronosis". Jet lag is classified as one of the circadian rhythm sleep disorders. In other words, jet lag arises from a transient misalignment of the endogenous circadian timing system with external time, for example as experienced after travelling in a jet plane across multiple time zones or by night shift workers (so-called "social jet lag"). The term "jet lag" as used herein includes "social jet lag" experienced by shift workers. In jet lag associated with travelling, the severity and extent of these symptoms depend on the direction and speed of travel and the number of time zones crossed.

In accordance with the present invention, the term "symptoms associated with jet lag" includes, without being limiting, decreased alertness, night-time sleep disruption, poor overall performance, impaired cognitive skills, loss of appetite, depressed mood, reduced psychomotor coordination and gastrointestinal disturbances.

In accordance with the present invention, the term "diseases associated with jet lag" includes, without being limiting, sleep disruption, depression, malignant cell growth, temporal lobe atrophy and cardiomyopathies.

Glucocorticoid levels vary in a particular rhythm within an organism. Under normal circumstances, i.e. without any external interference with the glucocorticoid biosynthesis, the time point of maximum amounts of glucocorticoids (also referred to herein as the glucocorticoid peak) occurs at a certain time of day, e.g. in humans said glucocorticoid peak is reached at approximately 8 am while in rodents the peak is observed around the beginning of the activity phase in the evening. The time point of maximum amounts of glucocorticoids in any given organism can be determined by methods well known in the art, such as for example the above mentioned methods of determining glucocorticoid levels including e.g. the determination by corticoid metabolite extraction from urine or feces and quantification by RIA (Abraham et al. 2006). By determining glucocorticoid levels at several time points during the day it is possible to derive the time point of maximum amounts of glucocorticoids within the organism analysed.

In accordance with the present invention, the administration of the modulator results in "a directional change of the time point of maximum amounts of glucocorticoids". In other words, the time point of maximum amounts of glucocorticoids occurs later or earlier than it would do in the absence of the modulator(s). In one embodiment, the amplitude of maximum glucocorticoid amounts is not altered upon administration of the modulator(s) of the invention. Whether the time point of maximum amounts of glucocorticoids has been altered to occur earlier or later can, for example, be confirmed by determining the time point of maximum amounts of glucocorticoids both in the absence and in the presence of the modulator(s), wherein a different time point of maximum amounts of glucocorticoids in the presence of the modulator(s) as compared to the time point of maximum amounts of glucocorticoids in the absence of the modulator(s) is indicative of a directional change of this time point.

Exemplary means of achieving a specific shift, i.e. either backward or forward, are described in more detail below. Thus, the modulator(s) of the present invention may be administered anytime between 1 and 14 days prior to initiating the activities that cause jet lag. It will be understood that the timing of administration may be at any interval between 1 day and 14 days, including but not limited to fractions of said intervals, such as at day 2, 3, 4, 5, 6, 7, 8, 9, 10, 11, 12, or 13 prior to initiating the activities that cause jet lag. In one embodiment, the modulator(s) of the present invention may be administered on the same day as initiating the activities that cause jet lag. It will be appreciated by the skilled person that the modulator(s) of the invention may also be administered at the time of initiating the activities that cause jet let or even after initiating them. In one embodiment, the modulator(s) of the present invention may be administered anytime between 1 and 4 days after to initiating the activities that cause jet lag. In one example, the modulator(s) may be administered e.g. when boarding a long-distance flight, such that the effect of the modulator(s) is already achieved at the time when jet-let would normally ensue, e.g. upon arrival at the destination. In the second case, i.e. administration after initiating the activities that cause jet lag, said administration may be suitable to ameliorate the symptoms associated with jet leg, even if the onset of jet lag may not be entirely prevented. Thus, for example, the duration or severity of jet lag may be decreased if, for example, the modulator(s) may be administered after travel/ arrival at the destination but at a time when the jet lag still persists.

Preferably, the modulator(s) are administered at least once. Furthermore, in order to achieve a shift towards an earlier time point than naturally occurring, a modulator such as e.g. an inhibitor of glucocorticoid biosynthesis may be administered before the time point of the naturally occurring peak (in humans e.g. around the time of starting the rest phase, e.g. upon going to bed). Alternatively, in order to achieve a shift towards a later time point than naturally occurring, a modulator such as e.g. an inhibitor of glucocorticoid biosynthesis may be administered during the time point of the naturally occurring peak (i.e. upon starting the active phase, in humans e.g. around the time of getting up in the morning). For example, in mice, administration of metyrapone, an inhibitor of glucocorticoid biosynthesis, at 9 am (first half of rest phase) resulted in a forward shift of the peak of maximum glucocorticoid levels while administration at 6 pm (i.e. in the first half of the active phase) resulted in a backward shift of the peak of maximum glucocorticoid levels. In humans, this would translate into an administration of metyrapone around midnight in order to achieve a forward shift and an administration around 9 to 10 am in order to achieve a backward shift. Of course these times will vary depending on the speed of release of the active compound, i.e. a slow release formulation may be employed for earlier administration.

It will be appreciated by the skilled person that in order to obtain a shift in the glucocorticoid peak time in accordance with the present invention, the modulator(s) may be active for a limited amount of time after administration, thus resulting in a reversible modulation of the target molecule. The modulator(s) preferably has/have a half-life sufficiently long to achieve a shift of the glucocorticoid peak time while not permanently interfering with glucocorticoid biosynthesis or degradation or receptor activity. Where a lead compound has been identified as a potential compound for developing a drug for preventing or treating symptoms and/or diseases associated with jet lag, or where a modulator in accordance with the present invention has been identified, said compounds may be further modified depending on the shift to be achieved. Thus, a shift of e.g. three hours may require that the compound has a different half-life after administration than the same compound for achieving a shift of merely one hour. Means and methods to modify a modulatory compound in order to alter its half-life or its bioavailability, such as e.g. transport to the target tissue, are well known to the person skilled in the art and include the above recited modification in order to achieve e.g. an altered degradation, or secretion of the compound. Successful alteration of the half-life of a particular compound can for example be tested in serum-stability assays as well as in in vivo models after administration. Such methods are part of the common general knowledge of the skilled person. As is detailed herein below, the length of treatment needed to achieve the intended shift following treatment and the particular amounts necessary to achieve this shift may be determined by conventional tests which are well known to the person skilled in the art.

In accordance with the present invention it was surprisingly found that shifting the rhythm of adrenal glucocorticoid amounts results in either accelerated or decelerated adaptation to the new time zone or the new work schedule. Thus, it was found that the adrenal circadian clock, through control of glucocorticoid rhythms, is a major regulator of reentrainment to jet lag. As is shown in the appended examples, timed application of metyrapone, an inhibitor of adrenal glucocorticoid synthesis, evoked a shift in the glucocorticoid rhythmicity and resulted in improved behavioral adaptation to the new time zone.

In accordance with the present invention, organ-specific expression profiles of key circadian clock genes were determined to characterize circadian resynchronization during jet lag at the molecular level. Each of the organs and clock genes examined showed a characteristic time course of adjustment from the pre- to the post-jet lag state. Therefore, jet lag evokes a global de-synchronization of clock gene expression rhythms that gradually returns to the robust alignment typical for the entrained state of the circadian oscillator system.

It was further shown that during this process the circadian clock of the adrenal gland has a special role in that adrenal clock-controlled glucocorticoids regulated the reentrainment of locomotor activity rhythms. By timed application of metyrapone prior to jet lag, the phase of the endogenous glucocorticoid rhythm was shifted, which in turn evoked a predictable change in the rate of behavioral reentrainment. The findings of the present invention not only substantiate the importance of glucocorticoid rhythms in jet lag adaptation, but also provide a novel therapeutic model for the treatment of jet lag and its associated symptoms.

It has previously been shown that the adrenal clock gates the response of the steroidogenic machinery to adrenocorticotropin and thereby influences the rhythm of glucocorticoid secretion into the blood (Oster et al. 2006; Son et al. 2008). Behavioral data further indicated a regulatory function of the adrenal circadian clock in behavioral reentrainment during jet lag. Together with the role of glucocorticoids in the resetting of peripheral oscillators (Balsalobre et al. 2000), these findings suggest a role for the adrenal clock in the overall circadian entrainment process (Schibler et al. 2003; Le Minh et al. 2001). Both the SCN and the adrenal clock receive direct photic input through the autonomic nervous system (Oster et al. 2006; Ishida et al. 2005), which might account for the rapid entrainment response of these oscillators.

Without wishing to be bound by any theory, it is hypothesised that the SCN signals primarily through neuronal connections to the adrenal, thereby regulating adrenal clock gene expression. In turn, the adrenal clock feeds back to the SCN, where it stabilizes SCN-controlled activity rhythms. Glucocorticoids are part of this adrenal to SCN feedback, which most likely uses indirect pathways of transmission, as SCN neurons themselves do not express glucocorticoid receptors (Balsalobre et al. 2000; Rosenfeld et al. 1988). Such a feedback control mechanism would prevent uncoordinated resetting of the circadian system, for example in response to sporadic light exposure, and thus serves as a protection from Zeitgeber noise. In the case of jet lag, however, this feedback loop becomes a problem, preventing rapid adaptation of behavioral rhythms to the new time zone. When the adrenal clock is compromised, for example by adrenalectomy (Sage et al. 2004) or transplantation of a clock-deficient adrenal, then adrenal-SCN feedback is affected. The SCN pacemaker thus becomes less resistant to external perturbation and hence more rapidly relays the external resetting signal to subordinated clocks and tissues, resulting in accelerated reentrainment.

Few studies have addressed glucocorticoid function in reentrainment during jet lag, focusing on the regulation of the amplitude (Sage et al. 2004; Mohawk et al. 2005) and phase (Sage et al. 2004) of diurnal glucocorticoid secretion. Sage et al. have shown that in adrenalectomized rats, exogenously provided glucocorticoid provided in a fluctuating pattern (rhythmic group) resulted in resynchronization within the same time frame as un-treated, non-adrenalectomized rats. However, these authors also showed that when the glucocorticoid rhythm was inverted relative to the LD cycle, overcompensation was seen, with decelerated reentrainment rates. Furthermore, an accelerated resynchronization was observed when rats where treated with steady-state levels of glucocorticoids (either low, medium or high glucocorticoids) as well as in the absence of glucocorticoids. The authors concluded that in the absence of glucocorticoid fluctuations the activity rhythms of the rats are directly dependent on the light-dark cycle (i.e. on the external rhythms) and are less dependent on the internal rhythms. Finally, the authors also concluded that cortisol has no significant effect on activity rhythms when given out of phase with the natural rhythm of this hormone.

Based on these findings in the art (e.g. Sage et al. 2004), a complete block of glucocorticoid production or the achievement of steady-state glucocorticoid levels would be considered as an approach for achieving accelerated reentrainment. However, adrenalectomy, as performed on the test animals in (Sage et al. 2004), would have the disadvantage of potentially having broader consequences than merely affecting behavioral resetting, since glucocorticoids have other functions, e.g. in immune regulation, and in addition to glucocorticoids, the adrenal produces several other hormones, such as mineralocorticoids and catecholamines. Recently it was shown that in clock-deficient mice, there was an abnormally high synthesis of aldosterone, which impaired the renin-angiotensin pathway of the kidney (Doi M, et al. Salt-sensitive hypertension in circadian clock-deficient Cry-null mice involves dysregulated adrenal Hsd3b6. Nat. Med. 2010; 16(1):67-74). Thus, the adrenal clock might be involved in a feedback loop not only with the SCN, but also with other organs, such as the kidney, thereby regulating kidney physiology.

Contrary to the findings of Sage et al., it was found in accordance with the present invention that chronopharmacologic manipulation of the glucocorticoid phase, i.e. a shifted rhythm of glucocorticoid secretion, prior to jet lag by timed administration of metyrapone was sufficient to substantially affect behavioral reentrainment and thus affect the duration of jet lag. Treatment by temporarily affecting glucocorticoid biosynthesis or degradation thus provides an improved treatment strategy as compared to complete blockage of glucocorticoid secretion, offering the advantage of minor side effects. Furthermore, since the particular glucocorticoid biosynthesis inhibitor used herein—metyrapone—is used in the diagnosis of adrenal insufficiency, its use in alleviating jet lag in humans is feasible.

In a preferred embodiment of the modulator(s) of the present invention, the glucocorticoid is selected from the group consisting of cortisol and corticosterone.

The term "cortisol", in accordance with the present invention, relates to a glucocorticoid produced by the adrenal gland in the zona fasciculata of the adrenal cortex having the structural formula:

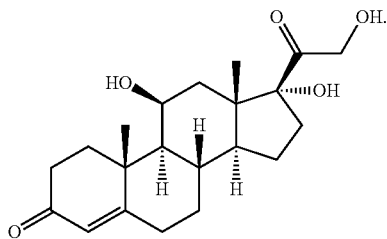

It is released in response to stress, or to a low level of blood glucocorticoids. Cortisol's primary functions in the body are increasing blood sugar through gluconeogenesis, suppressing the immune system and aiding in fat, protein, and carbohydrate metabolism. The amount of cortisol hormone present in the blood undergoes diurnal variation, with the highest levels present in the early morning (approximately 8 am), and the lowest levels present around 12-4 am, or 3-5 hours after the onset of sleep.

In accordance with the present invention, the term "corticosterone" relates to a 21-carbon steroid hormone of the corticosteroid type produced in the cortex of the adrenal glands having the structural formula:

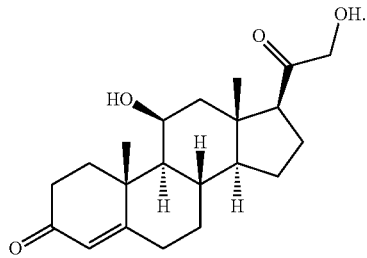

In humans, corticosterone is produced in only small amounts primarily in the zona fasciculata of the adrenal cortex and is believed to have only weak glucocorticoid and mineralocorticoid potencies. Its primary role is thought to be as an intermediate in the steroidogenic pathway from pregnenolone to aldosterone.

In another preferred embodiment, the modulator(s) may be administered in a pharmaceutical composition.

The term "pharmaceutical composition", as used herein, relates to a composition for administration to a patient, preferably a human patient. The pharmaceutical composition of the invention comprises at least one, such as at least two, e.g. at least three, in further embodiments at least four such as at last five of the above mentioned modulators of the present invention and may, optionally, comprise further molecules capable of altering the characteristics of the compounds of the invention thereby, for example, stabilizing or de-stabilizing, modulating and/or inhibiting or activating their function. The invention also envisages mixtures of the modulators of the invention. In cases where more than one modulator is comprised in the pharmaceutical composition it is understood that none of these compounds has any essentially inhibitory effect on the other compounds also comprised in the composition.

The composition may, for example, be in solid or liquid form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. The skilled person knows that the effective amount of a pharmaceutical composition administered to an individual will, inter alia, depend on the nature of the compound. For example, if said compound is a polypeptide or protein, the total pharmaceutically effective amount of pharmaceutical composition administered parenterally per dose will be in the range of about 1 µg protein/kg/day to 10 mg protein/kg/day of patient body weight, although, as noted above, this will be subject to therapeutic discretion. More preferably, this dose is at least 0.01 mg protein/kg/day, and most preferably for humans between about 0.01 and 1 mg protein/kg/day. Furthermore, if for example said compound is an iRNA agent, such as an siRNA, the total pharmaceutically effective amount of pharmaceutical composition administered will typically be less than about 75 mg per kg of body weight, such as for example less than about 70, 60, 50, 40, 30, 20, 10, 5, 2, 1, 0.5, 0.1, 0.05, 0.01, 0.005, 0.001, or 0.0005 mg per kg of body weight. More preferably, the amount will be less than 2000 nmol of iRNA agent (e.g., about 4.4×1,016 copies) per kg of body weight, such as for example less than 1,500, 750, 300, 150, 75, 15, 7.5, 1.5, 0.75, 0.15, 0.075, 0.015, 0.0075, 0.0015, 0.00075 or 0.00015 nmol of iRNA agent per kg of body weight.

The length of treatment needed to observe changes and the interval following treatment for responses to occur vary depending on the desired effect. The particular amounts may be determined by conventional tests which are well known to the person skilled in the art.

Pharmaceutical compositions of the invention may be administered orally, rectally, parenterally, intracisternally, intraperitoneally, topically (as by powders, ointments, drops or transdermal patch), bucally, or as a nasal spray.

The present invention further relates to a method of preventing or treating symptoms and/or diseases associated with jet lag comprising administering a pharmaceutically effective amount of a modulator of glucocorticoid biosynthesis and/or a modulator of glucocorticoid degradation and/or a modulator of glucocorticoid receptor activity to a subject in need thereof, wherein administration of the modulator(s) to a subject results in a directional change of the time point of maximum amounts of glucocorticoid in the subject as compared to the time point of maximum amounts of glucocorticoid in a subject not treated with the modulator(s).

The definitions as well as the preferred embodiments provided herein above with regard to the main embodiment apply mutatis mutandis also to this embodiments relating to a method of preventing or treating symptoms and/or diseases associated with jet lag.

In a further preferred embodiment of the modulator or the method of the present invention, the modulator(s) is/are selected from the group consisting of a small organic molecule, an antibody or a fragment or derivative thereof, an aptamer, an siRNA, an shRNA, an miRNA, a ribozyme, or an antisense nucleic acid molecule.

It will be appreciated by the skilled person that inhibitory molecules, such as siRNA, shRNA etc. can also act as activators of e.g. glucocorticoid degradation, in accordance with the present invention, for example in cases where these inhibitory molecules down-regulate the expression of (a) molecule(s) normally preventing glucocorticoid degradation, such as for example transcortin.

A "small molecule" according to the present invention may be, for example, an organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources. Organic compounds can be natural or synthetic. Alternatively, the "small molecule" in accordance with the present invention may be an inorganic compound. Inorganic compounds are derived from mineral sources and include all compounds without carbon atoms (except carbon dioxide, carbon monoxide and carbonates). Preferably, the small molecule has a molecular weight of less than about 2,000 amu, or less than about 1,000 amu such as less than about 500 amu, and even more preferably less than about 250 amu. The size of a small molecule can be determined by methods well-known in the art, e.g., mass spectrometry. The small molecules may be designed, for example, based on the crystal structure of the target molecule, where sites presumably responsible for the biological activity, can be identified and verified in in vivo assays such as in vivo high-throughput screening (HTS) assays.

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments as well as Fd, F(ab')$_2$, Fv or scFv fragments, single domain antibodies etc; see, for example Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also includes embodiments such as chimeric (human constant domain, non-human variable domain), single chain and humanized (human antibody with the exception of non-human CDRs) antibodies.

Various techniques for the production of antibodies are well known in the art and described, e.g. in Harlow and Lane (1988) and (1999), loc. cit. Thus, the antibodies can be produced by peptidomimetics. Further, techniques described for the production of single chain antibodies (see, inter alia, U.S. Pat. No. 4,946,778) can be adapted to produce single chain antibodies specific for the target of this invention. Also, transgenic animals or plants (see, e.g., U.S. Pat. No. 6,080,560) may be used to express (humanized) antibodies specific for the target of this invention. Most preferably, the antibody is a monoclonal antibody, such as a human or humanized antibody. For the preparation of monoclonal antibodies, any technique which provides antibodies produced by continuous cell line cultures can be used. Examples for such techniques are described, e.g. in Harlow and Lane (1988) and (1999), loc. cit. and include the hybridoma technique originally described by (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, inter alia, bacteriophages, viruses or plasmid vectors.

Aptamers are nucleic acid molecules or peptide molecules that bind a specific target molecule. Aptamers are usually created by selecting them from a large random sequence pool, but natural aptamers also exist in riboswitches. Aptamers can be combined with ribozymes to self-cleave in the presence of their target molecule. More specifically, aptamers can be classified as nucleic acid aptamers, such as DNA or RNA aptamers, or peptide aptamers. Whereas the former normally consist of (usually short) strands of oligonucleotides, the latter preferably consist of a short variable peptide domain, attached at both ends to a protein scaffold.

Nucleic acid aptamers are nucleic acid species that, as a rule, have been engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers usually are peptides or proteins that are designed to interfere with other protein interactions inside cells. They consist of a variable peptide loop attached at both ends to a protein scaffold. This double structural constraint greatly increases the binding affinity of the peptide aptamer to levels comparable to an antibody's binding affinity (nanomolar range). The variable peptide loop typically comprises 10 to 20 amino acids, and the scaffold may be any protein having good solubility properties. Currently, the bacterial protein Thioredoxin-A is the most commonly used scaffold protein, the variable peptide loop being inserted within the redox-active site, which is a -Cys-Gly-Pro-Cys- loop in the wild protein, the two cysteins lateral chains being able to form a disulfide bridge. Peptide aptamer selection can be made using different systems, but the most widely used currently is the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. Unmodified aptamer applications currently focus on treating transient conditions such as blood clotting, or treating organs such as the eye where local delivery is possible. This rapid clearance can be an advantage, for example if a minor shift of the time point of maximum amounts of glucocorticoid is aimed at. Several modifications, such as 2'-fluorine-substituted pyrimidines, polyethylene glycol (PEG) linkage, fusion to albumin or other half life extending proteins etc. are available to scientists such that the half-life of aptamers can be adjusted to achieve the intended shift in the glucocorticoid peak.

The term "peptide" as used herein describes a group of molecules consisting of up to 30 amino acids, whereas the term "protein" as used herein describes a group of molecules consisting of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "protein" (wherein "protein" is interchangeably used with "polypeptide") also refer to naturally modified peptides/proteins wherein the modification is effected e.g. by glycosylation, acetylation, phosphorylation and the like. Such modifications are well-known in the art.

In accordance with the present invention, the term "small interfering RNA (siRNA)", also known as short interfering RNA or silencing RNA, refers to a class of 18 to 30, preferably 19 to 25, most preferred 21 to 23 or even more preferably 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

siRNAs naturally found in nature have a well defined structure: a short double-strand of RNA (dsRNA) with 2-nt 3' overhangs on either end. Each strand has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Essentially any gene of which the sequence is known can thus be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Exogenously introduced siRNAs may be devoid of overhangs at their 3' and 5' ends, however, it is preferred that at least one RNA strand has a 5'- and/or 3'-overhang. Preferably, one end of the double-strand has a 3'-overhang from 1 to 5 nucleotides, more preferably from 1 to 3 nucleotides and most preferably 2 nucleotides. The other end may be blunt-ended or has up to 6 nucleotides 3'-overhang. In general, any RNA molecule suitable to act as siRNA is envisioned in the present invention. The most efficient silencing was so far obtained with siRNA duplexes composed of 21-nt sense and 21-nt antisense strands, paired in a manner to have a 2-nt 3'-overhang. The sequence of the 2-nt 3' overhang makes a small contribution to the specificity of target recognition restricted to the unpaired nucleotide adjacent to the first base pair (Elbashir et al. 2001). 2'-deoxynucleotides in the 3' overhangs are as efficient as ribonucleotides, but are often cheaper to synthesize and probably more nuclease resistant. Delivery of siRNA may be accomplished using any of the methods known in the art, for example by combining the siRNA with saline and administering the combination intravenously or intranasally or by formulating siRNA in glucose (such as for example 5% glucose) or cationic lipids. Also polymers can be used for siRNA delivery in vivo through systemic routes either intravenously (IV) or intraperitoneally (IP) (Fougerolles et al. (2008), *Current Opinion in Pharmacology*, 8:280-285; Lu et al. (2008), Methods in Molecular Biology, vol. 437: Drug Delivery Systems—Chapter 3: Delivering Small Interfering RNA for Novel Therapeutics).

A short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. si/shRNAs to be used in the present invention are preferably chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Further molecules effecting RNAi include, for example, microRNAs (miRNA). Said RNA species are single-stranded RNA molecules which, as endogenous RNA molecules, regulate gene expression. Binding to a complementary mRNA transcript triggers the degradation of said mRNA transcript through a process similar to RNA interference. Accordingly, miRNA may be employed as an inhibitor of glucocorticoid synthesis.

A ribozyme (from ribonucleic acid enzyme, also called RNA enzyme or catalytic RNA) is an RNA molecule that catalyses a chemical reaction. Many natural ribozymes catalyze either their own cleavage or the cleavage of other RNAs, but they have also been found to catalyze the aminotransferase activity of the ribosome. Non-limiting examples of well-characterized small self-cleaving RNAs are the hammerhead, hairpin, hepatitis delta virus, and in vitro-selected lead-dependent ribozymes, whereas the group I intron is an example for larger ribozymes. The principle of catalytic self-cleavage has become well established in the last years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each usually with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

A recent development, also useful in accordance with the present invention, is the combination of an aptamer recognizing a small compound with a hammerhead ribozyme. The conformational change induced in the aptamer upon binding the target molecule is supposed to regulate the catalytic function of the ribozyme.

The term "antisense nucleic acid molecule" is known in the art and refers to a nucleic acid which is complementary to a target nucleic acid. An antisense molecule in accordance with the invention is capable of interacting with the target nucleic acid, more specifically it is capable of hybridizing with the target nucleic acid. Due to the formation of the hybrid, transcription of the target gene(s) and/or translation of the target mRNA is reduced or blocked. Standard methods relating to antisense technology have been described (see, e.g., Melani et al., Cancer Res. (1991) 51:2897-2901).

In a further preferred embodiment of the modulator(s) or the method of the invention, the symptoms and/or diseases associated with jet lag are selected from the group consisting of sleep disruption, impaired cognitive skills, loss of appetite, depression, reduced psychomotor coordination, gastrointestinal disturbances, decreased alertness, malignant cell growth, temporal lobe atrophy and cardiomyopathies.

The term "sleep disruption", in accordance with the present invention, relates to a sleeping disorder associated with difficulties initiating and/or maintaining sleep at normal times during a day. Sleep disruption is often associated with a desynchronisation of the body's internal clock and is thus often followed by functional impairment while awake. Sleep disruption may either be secondary to another condition or may be primary—e.g. primary insomnia—that is not attributable to another medical, psychiatric, or environmental cause.

In accordance with the present invention, the term "impaired cognitive skills" refers to an impairment in the efficiency of the brain to receive and process data and form memories. Cognitive impairment is also seen in various diseases of the central nervous system including major depression, Alzheimer's, Parkinson's, schizophrenia, chronic stress as well as numerous genetic disorders.

The term "loss of appetite", as used herein, relates to a reduction in appetite for food and/or drinks, which may cause an unintentional weight loss.

As used herein, the term "depression" relates to a mental disorder characterised by a low mood usually accompanied by low self-esteem and by loss of interest or pleasure in normally enjoyable activities. Depressed people may have thoughts and feelings of worthlessness, inappropriate guilt or regret, helplessness, hopelessness, and self-hatred. In severe cases, depressed people may have symptoms of psychosis. These symptoms include delusions or, less commonly, hallucinations, usually unpleasant. Other symptoms of depression include poor concentration and memory, withdrawal from social situations and activities, reduced sex drive, and thoughts of death or suicide.

In accordance with the present invention, the term "reduced psychomotor coordination" relates to a reduction in motor-coordination, i.e. a reduced rate of coordinated movement in response to a stimulus and the processing thereof, such as e.g. is required in navigating traffic.

The term "gastrointestinal disturbances", in accordance with the present invention, relates to symptoms and diseases that pertain to the gastrointestinal tract. This includes disturbances and diseases of the esophagus, stomach, first, second and third part of the duodenum, jejunum, ileum, the ileo-cecal complex, large intestine (ascending, transverse and descending colon) sigmoid colon and rectum. Examples of "gastrointestinal disturbances" include, without being limiting disorders of the upper gastrointestitnal tract, such as disorders of the esophagus (e.g. esophagitis, gastroesophageal reflux disease (GERD), laryngopharyngeal reflux, Boerhaave syndrome, Mallory-Weiss syndrome, Zenker's diverticulum, Barrett's esophagus, esophageal motility disorder, esophageal stricture, megaesophagus) or the stomach (e.g. gastritis, peptic (gastric) ulcer, dyspepsia, pyloric stenosis, achlorhydria, gastroparesis, gastroptosis, portal hypertensive gastropathy, gastric antral vascular ectasia, gastric dumping syndrome); intestinal disorders, such as disorders of the small and/or large intestine (e.g. enteritis, peptic (duodenal) ulcer, coeliac disease, tropical sprue, blind loop syndrome, Whipple's disease, short bowel syndrome, Steatorrhea, Milroy disease, appendicitis, colitis, functional colonic disease, megacolon/toxic megacolon, diverticulitis/diverticulosis, enterocolitis, inflammatory bowel disease (Crohn's disease), abdominal angina, mesenteric ischemia, angiodysplasia, bowel obstruction, constipation, Diarrhea) or disorders of the rectum and anus (e.g. proctitis, proctalgia fugax, rectal prolapse, anal fissure/anal fistula, anal abscess); accessory digestive glands diseases such as disorders of the liver (hepatitis, cirrhosis, fatty liver, hepatic veno-occlusive disease, portal hypertension, nutmeg liver, alcoholic liver disease, liver failure, liver abscess, hepatorenal syndrome, peliosis hepatis, hemochromatosis, Wilson's disease), disorders of the pancreas (e.g. pancreatitis, pancreatic pseudocyst, exocrine pancreatic insufficiency, pancreatic fistula), disorders of the gall bladder and bile ducts (e.g. cholecystitis, gallstones/cholecystolithiasis, cholesterolosis, Rokitansky-Aschoff sinuses, postcholecystectomy syndrome cholangitis, cholestasis/Mirizzi's syndrome, biliary fistula, haemobilia, gallstones/cholelithiasis); as well as hernias, gastrointestinal bleeding and peritonitis.

In accordance with the present invention, the term "decreased alertness" refers to a state in which a person is not fully awake, aware of, or able to respond normally to his or her external environment. Decreased alertness can be the consequence of sleep disruption (see above) but is also a symptom of several diseases of the central nervous system such as Alzheimer's, major depression etc.

The term "malignant cell growth" (also referred to herein as cancer), in accordance with the present invention, refers to a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system).

As used herein, the term "temporal lobe atrophy" relates to a partial or complete loss of tissue of the temporal lobe, which is a region located in the cerebral cortex. Such symptoms are often associated with CNS degenerative diseases such as Alzheimer's or dementia.

In accordance with the present invention, the term "cardiomyopathies" relates to a deterioration of the function of the myocardium, i.e. the heart muscle. Non-limiting examples of cardiomyopathies include extrinsic cardiomyopathies such as e.g. congenital heart disease, ischemic (or non-ischaemic) cardiomyopathy, hypertensive cardiomyopathy, valvular cardiomyopathy, inflammatory cardiomyopathy (including Chagas disease), cardiomyopathy secondary to a systemic metabolic disease, alcoholic cardiomyopathy, diabetic cardiomyopathy, restrictive cardiomyopathy; as well as intrinsic cardiomyopathies, such as e.g. dilated cardiomyopathy (DCM), hypertrophic cardiomyopathy (HCM or HOCM), arrhythmogenic right ventricular cardiomyopathy (ARVC), restrictive cardiomyopathy (RCM) and noncompaction cardiomyopathy.

In a more preferred embodiment of the modulator(s) or the method of the present invention, the amplitude of maximum glucocorticoid amounts is not significantly altered.

The term "amplitude of maximum glucocorticoid amounts" in accordance with the present invention relates to the amount of glucocorticoid that is secreted at the time point of maximum glucocorticoid amounts present in the subject, i.e. at the glucocorticoid peak. In accordance with this preferred embodiment, this amount of glucocorticoid present at the time point of the glucocorticoid peak is not, or is not significantly altered after administration of the modulator(s) as compared to the amount of glucocorticoid present at the time point of the glucocorticoid peak in the absence of the modulator(s). Preferably, the amount of glucocorticoid is determined over the entire breadth of the peak, i.e. as the area-under-curve. It is preferred that a minimum of two measurements are carried out to determine the amount of glucocorticoid, preferably once in the morning and once in the evening. More preferably, more regular measurements are carried out at the time of the glucocorticoid peak, such as for example at least every two hours between 4 am and 11 am for humans. More preferably, measurements are carried out every hour, such as for example every 30 minutes or even more preferably every 15 minutes. Such determination methods are well known in the art.

The amount of glucocorticoid is considered not to be significantly altered when it differs only by an amount that represents variations due to the limitations in sensitivity in the methods employed for measurement or variations endogenously occurring within said subject. Thus, it is considered to be significantly altered when it differs for example by more than $2\sigma$, i.e. two-times the standard deviation of the amount of glucocorticoid when repeatedly (i.e. at least two times) measured within the same individual at the peak time and in the absence of the modulator(s). Alternatively, the amplitude of maximum glucocorticoid amounts after administration of the modulator(s) preferably differs from the amplitude of maximum glucocorticoid amounts in the absence of the modulator(s) by less than 30%, such as for example less than 20%, more preferably less than 10%, such as for example less than 5% and even more preferably less than 2%. Most preferably, the amount of glucocorticoid is considered not to be significantly altered when the variation does not exceed the endogenously occurring variation within the subject. Methods of determining the naturally occurring variations within a subject are well known in the art and include, without being limiting, the determination of glucocorticoid levels in the absence of the modulator(s) of the invention at the peak time for several, such as for example at least two, such as at least three, such as at least four days for said subject and deriving the minimum and maximum amount of glucocorticoid level within said subject at the peak time.

In another preferred embodiment of the modulator(s) or the method of the invention, the time point of maximum amounts of glucocorticoids in a subject treated with the modulator(s) is earlier than the time point of maximum amounts of glucocorticoids in a subject not treated with the modulator(s) and this earlier time point results from the administration of the modulator(s) in the first half of the rest phase of the subject to be treated.

In accordance with this embodiment, the time point of maximum amounts of glucocorticoids is shifted towards an earlier time point as compared to the time point of maximum amounts of glucocorticoids observed in the absence of the modulator(s). This shift is also referred to herein as forward shift. In other words, in a human normally having the time point of maximum amounts of glucocorticoids around 8 am, said time point is shifted to an earlier time such as for example 7 am, 6 am, 5 am, 4 am etc.

The term "the first half of the rest phase of the subject" as used herein refers to the time point of going to bed as well as the first hours of sleep, including at least the first hour of sleep, such as for example at least the first two hours of sleep, more preferably at least the first three hours of sleep and most preferably at least the first four hours of sleep. Means and methods to administer (a) modulator(s) in accordance with the present invention while the subject to be treated is sleeping are well known to the person skilled in the art and include, without being limiting, capsules and tablets for oral administration as well as skin patches or creams for topical application or gaseous preparations for inhalation which provide a delayed or sustained release of the active compounds over a prolonged period of time, such as the above recited times of sleep.

Such a forward shift is advantageous for example when travelling east-bound or when working a shift that starts earlier than the normal working time of the respective individual. Due to the earlier sunrise or the earlier waking up of the shift worker, the time span between waking and the naturally occurring glucocorticoid peak is increased, thus causing the onset of jet-lag. In accordance with the present invention it was now found that the administration of a modulator of glucocorticoid biosynthesis, such as for example an inhibitor of glucocorticoid biosynthesis such as metyrapone, during the first half of the rest phase of the subject (e.g. at the time of going to bed prior to travelling or commencing shift work) achieves such a forward shift of maximum glucocorticoid amounts and thus shortens jet lag as it brings the individuals circadian clock into closer analogy with external time.

In another preferred embodiment of the modulator(s) or the method of the invention, the time point of maximum amounts of glucocorticoids in a subject treated with the modulator(s) is later than the time point of maximum amounts of glucocorticoids in a subject not treated with the modulator(s) and this later time point results from the administration of the modulator(s) in the first half of the active phase of the subject to be treated.

In accordance with this embodiment, the time point of maximum amounts of glucocorticoids is shifted towards a later time point as compared to the time point of maximum amounts of glucocorticoids observed in the absence of the modulator(s). This shift is also referred to herein as backward shift. In other words, in a human normally having the time point of maximum amounts of glucocorticoid around 8 am, said time point is shifted to a later time such as for example 9 am, 10 am, 11 am etc.

The term "the first half of the active phase of the subject" as used herein refers to the time point after waking up, including getting up and starting activities. The term includes at least the first hour after waking up, such as for example at least the first two hours after waking up, more preferably at least the first three hours after waking up and most preferably at least the first four hours after waking up.

Such a backward shift is advantageous for example when travelling west-bound or when working a shift that starts later than the normal working time of the respective individual. Due to the later sunrise or the later waking up of the shift worker, the time span between waking and the naturally occurring glucocorticoid peak is decreased, thus causing the onset of jet-lag. In accordance with the present invention it was now found that the administration of a modulator of glucocorticoid biosynthesis, such as for example an inhibitor of glucocorticoid biosynthesis such as metyrapone, during the first half of the active phase of the subject (e.g. at or around the time of waking up prior to travelling or commencing shift work) achieves such a backward shift of maximum glucocorticoid amounts and thus shortens jet lag as it brings the individuals circadian clock into closer analogy with external time.

As shown in the appended examples, the molecular response of the mouse circadian system in an established experimental paradigm for jet lag was analysed whereby mice entrained to a 12-hour light/12-hour dark cycle undergo light phase advancement by 6 hours. Manipulation of the adrenal circadian clock, in particular phase-shifting of adrenal glucocorticoid rhythms, regulated the speed of behavioural reentrainment. Blocking adrenal glucocorticoid either prolonged or shortened jet lag, depending on the time of administration. Without wishing to be bound by theory, the present inventors consider this key role of adrenal glucocorticoid phasing for resetting of the circadian system as a novel approach for therapies for jet lag and jet lag-associated diseases.

In a further preferred embodiment of the modulator(s) or the method of the invention, the modulator(s) may be administered at least one time to the subject prior to and/or at the time of initiating activities that cause jet lag.

The term "at least one time" encompasses the administration of the inhibitor once, but also for example twice, three times, four times, five times, six times, seven times, eight times, nine times or ten times. The term also encompasses administrations of more than ten times.

In accordance with this embodiment, the modulator is to be administered prior to the time of initiating the activities that cause jet lag or at the time of initiating them. For example, in the case of long-distance travelling, the modulator(s) may be administered one day and/or several days before starting to travel, such as for example two days, three days, four days, five days, six days, seven days, eight days, nine days, ten days or even more than ten days before travelling. When the modulator(s) of the invention are to be administered more than once prior to initiating activities that cause jet lag, then the time point of administration might be adjusted gradually e.g. by administering the first dose for example during the time of peak, the second dose 1 hour after the peak time, the third dose 2 hours after the peak time etc. Similar considerations also apply to forward shifts requiring administration before the peak time. Alternatively, the modulator(s) may be administered at the time of starting to travel, for example when boarding the plane.

Preferably, administration is prior to initiating the activities that cause jet lag.

In a further preferred embodiment of the modulator(s) or the method of the invention, the modulator(s) are to be administered once a day.

In another preferred embodiment of the modulator of the invention, the modulator is selected from the group consisting of metyrapone, α-keto-konazole or any one of the inhibitors referred to in table 1 above. Most preferably, the modulator is metyrapone.

Metyrapone is an inhibitor of endogenous adrenal corticosteroid synthesis as it inhibits adrenal 11β-hydroxylase, an enzyme that converts 11-deoxycorticosterone to corticosterone. The chemical name of metyrapone is 2-methyl-1,2-di-3-pyridyl-1-propanone, and its structural formula is:

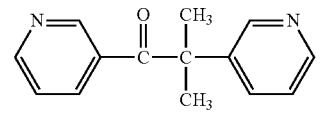

Unless otherwise defined, all technical and scientific terms used herein have the same meaning as commonly understood by one of ordinary skill in the art to which this invention belongs. In case of conflict, the patent specification, including definitions, will prevail.

EXAMPLES

Example 1

Material and Methods

Animals. For all experiments, male WT (C57BL/6J) and homozygous Per2/Cry1 double mutant mice (Per2tm1Brd; Zheng B, et al. The mPer2 gene encodes a functional component of the mammalian circadian clock. Nature. 1999; 400(6740):169-173; and Cry1tm1Jhjh; van der Horst G T, et al. Mammalian Cry1 and Cry2 are essential for maintenance of circadian rhythms. Nature. 1999; 398(6728):627-630) of 2-3 months of age were used as described previously (Oster et al. 2002). All animal experiments were done with prior permission from the Office of Consumer Protection and Food Safety of the State of Lower Saxony and in accordance with the German Law of Animal Welfare. Mice were housed in small groups of 5 or fewer under LD cycle conditions of 12 hours light, 12 hours dark, with food and water ad libitum.

Behavioral analysis. Handling and activity measurements during experiments were performed as described previously (Jud et al. 2005). Wheel-running activity was analyzed using ClockLab software (Actimetrics). For the jet lag experiment (6-hour rapid advance or 8-hour rapid delay of the LD cycle), animals were single-housed in running wheel-equipped cages for 2 weeks or longer under LD conditions (lights on, $ZT_0$; light intensities of 350 lux). On day 1 of the jet lag, the lights-off time ($ZT_{12}$) was shifted from 6 pm to 12 am (phase advance paradigm) or from 6 pm to 2 am (phase delay paradigm). Using a short day protocol, we defined day 1 as the first advanced dark period (similar to Davidson et al. 2009, who used a short night approach in which the first day is defined by the deemed light period; but different from Yamazaki et al. 2000, where the following day—corresponding to day 2 in our study—was referred to as day 1). For the delay experiment (8-hour rapid delay of the LD cycle), animals were housed in running wheel-equipped single cages for 2 weeks or longer under LD conditions (lights on, $ZT_0$; light intensities of 50 lux). On day 1 of the jet lag, the lights-off time ($ZT_{12}$) was shifted from 12 pm to 8 pm. Day 1 was defined here as the day with the first delayed dark period. Animals were synchronized to the new LD regimen for another 2 weeks during which time of wheel-running activity was recorded. Individual activity onsets before and after the shift were determined by visual inspection and averaged over the whole cohort to asses reentrainment rates.

qPCR. Animals were sacrificed at the indicated time points by cervical dislocation before (day 0) and at 4 different days after the phase advance of the LD cycle. Eyes were removed prior to tissue dissection under a 15-W red safety light at time points during the dark phase (Albrecht et al. 1997). Tissue samples were dissected and stored frozen in RNAlater (Ambion). Total RNA samples from adrenal, kidney, liver, and pancreas were prepared using RNeasy Micro and Mini Kits (Qiagen). cDNA was synthesized using Thermoscript RT Kit (Invitrogen). qPCR was performed on an iCycler thermocycler (Bio-Rad) with iQ SYBR Green Supermix (Bio-Rad) according to the manufacturer's protocol. Primer sequences and cycle conditions were as detailed previously (Oster et al. 2006; Oster et al. 2006(a)). Ef1α was used as standard, and single-well amplification efficiency estimates and relative quantification of expression levels were performed as described previously (Ramakers et al. 2003).

ISH. In situ hybridization. Animals were sacrificed 1 day before (day 0) and at days 2, 3, 4, and 12 after the LD shift, and brains were dissected. Tissues were fixed, dehydrated, and paraffin embedded; 8-µm sections were prepared (Jakubcakova et al. 2007) and stored at −80° C. Sections were hybridized with 35S-UTP-labeled antisense RNA probes for clock gene transcripts (Oster et al. 2006). Relative quantification of expression levels was performed by densitometric analysis of autoradiograph films using Scion Image software (Scion Corp.; Oster et al. 2002).

Adrenal Transplantations. Transplantations of adrenal fragments were performed as described previously (Oster et al. 2006; Musholt et al. 2002). Briefly, male WT and Per2/Cry1 double mutant mice of 6-8 weeks were anesthetized by i.p. injection of 100 mg/kg ketamine and 10 mg/kg xylazine. Adrenals were dissected from mutant animals following medial laparotomy and transplanted underneath the capsule of the kidney of an adrenalectomized WT host animal. Both adrenals were transplanted into a single host. To control for the transplantation procedure, WT animals received their own (i.e., WT) adrenal transplants following adrenalectomy. After the surgery, animals were allowed to recover for 8 weeks under standard LD conditions to ensure complete reinnervation of the transplanted tissues (Ulrich-Lai and Engeland 2000).

Hormone Measurements. Fecal samples were collected at 4-hour intervals before and after the jet lag treatment using wheel cages equipped with wire grid floors. To rule out stress-induced effects, animals were transferred to the collection cages 3 days prior to the first sampling interval. Fecal samples were stored at −80° C. Corticoid metabolite extraction and quantification by RIA (MP Biomedicals) were performed as described previously (Abraham et al. 2006).

Pharmacologic Treatments. Administration of metyrapone (Sigma-Aldrich) to WT mice was done for 16 days prior to the jet lag procedure (see above). Two sets of 24 animals each received metyrapone dissolved in water (100 mg/kg body weight per day) via i.p. injection at different times during the day. Injections were stopped 1 day before the LD shift (day 0). MET$_S$ animals were injected during the first half of their rest phase at $ZT_3$; MET$_N$ animals received metyrapone injections at the beginning of their activity phase at $ZT_{12}$. At day 16 of the treatment (day −1 relative to LD shift), fecal samples were collected to analyze the phase shift of corticoid excretion rhythms. Saline-treated (0.9% NaCl) WT littermates injected at $ZT_3$ or $ZT_{12}$ were used as controls for all experiments.

Statistics. Peak time analyses were performed using Prism software (GraphPad). A sine wave equation, y=BaseLine+Amplitude sin(frequency x+PhaseShift), was fitted to the data. For gene expression and corticosterone data, frequency was fixed to 24 hours. Maxima were calculated using the axis section of the second derivative. To determine $PS_{50}$, a sigmoid dose-response curve with variable slope was fitted to the sine wave maxima (corticosterone), y=Bottom+(Top−Bottom) (1+10(log PS50−x) HillSlope), or onset time points (locomotor activity) for each group. To test whether the best-fit $PS_{50}$ values differed between data sets, data were compared by extra sum-of-squares F test using a P value of less than 0.05 as a threshold. Maxima of gene expression or corticosterone at specific days were compared by Mann-Whitney rank sum test, even if normality tests and equal variance tests were positive, reflecting the small sample sizes of 3-9. A statistically significant difference was assumed with P values less than 0.05. Correlations between phase-shift activity onsets and corticosterone maxima were performed using linear regression. The quality of fit was estimated by r determination. Departure from linearity was tested with runs test. Normality and homoscedasticity tests were passed for all data sets. Diurnal variation of expression data was tested using Fourier analysis with CircWave version 3.3 software (Oster et al. 2006) and threshold values of 0.05 for α and a period of 24 hours.

Example 2

Differential Response of Circadian Clock Gene Expression in the SCN During Jet Lag Mice were entrained to a light-dark (LD) cycle of 12 hours light, 12 hours dark. Their running-wheel activity was restricted to the dark phase (Zeitgeber time 12 to 24; $ZT_{12}$-$ZT_{24}$), as expected for nocturnal animals. Advancing the LD cycle by 6 hours (which simulates eastward traveling) evoked a gradual adaptation of running-wheel activity to the changed light regimen. This transition was completed after 8-9 days (FIG. 1A). We determined locomotor activity onsets before and after the shift. Onset resetting followed a sigmoid curve, and a 50% phase shift ($PS_{50}$) was reached at 4.0±0.1 days (FIG. 1B).

Figure 2:
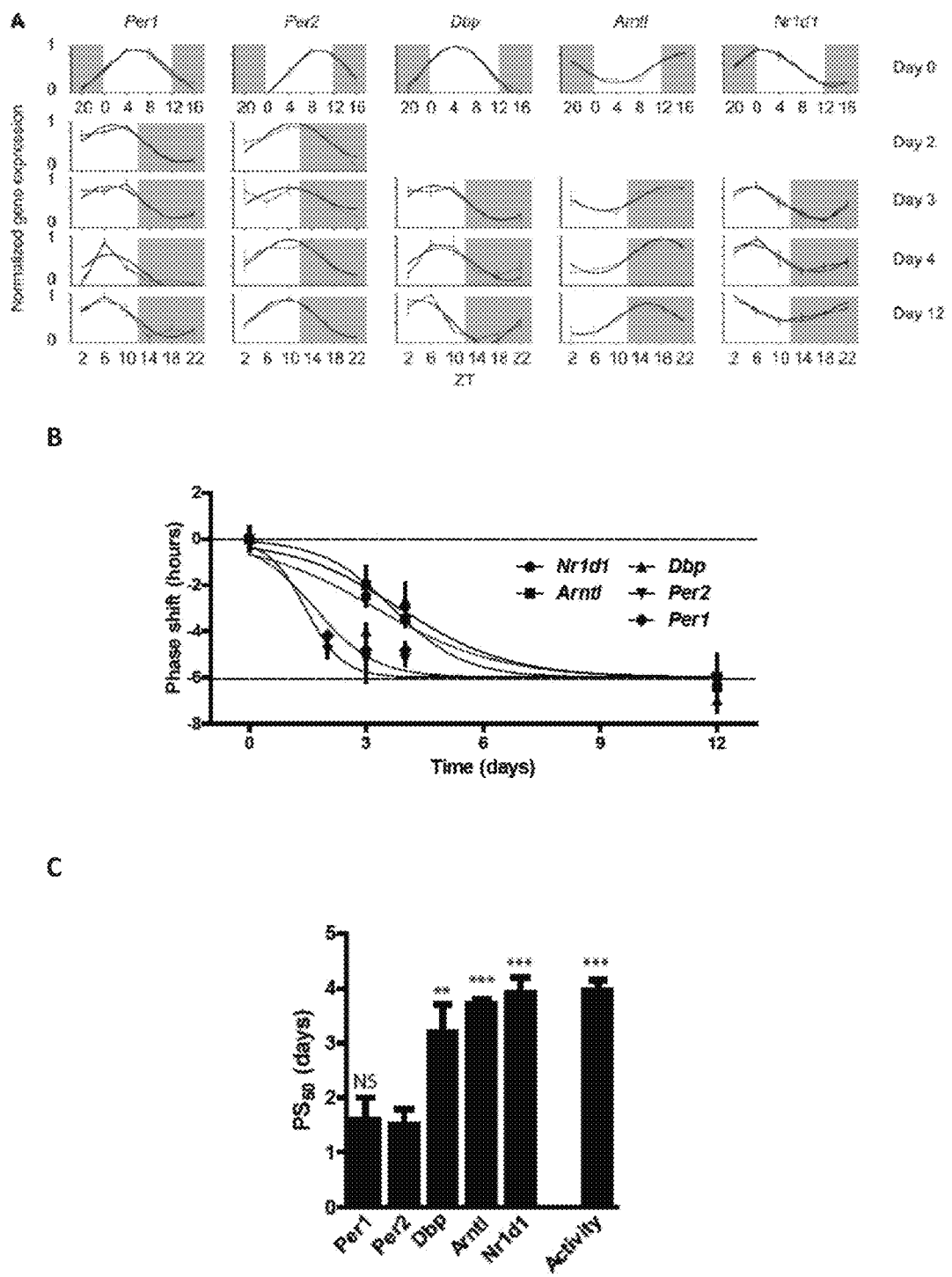
FIG. 2: Resetting of clock genes during jet lag in the SCN. (A) Diurnal mRNA profiles (average±SEM) of 5 different clock genes at days 0, 2, 3, 4, and 12 after the LD shift, superimposed with sine wave fits (black). Dark phases are marked by gray shading. Three (3) animals were used per time point. (B) Shifts of gene expression peak times obtained from the ISH data in FIG. 2A showed that adaptation to the new light schedule varied for the 5 clock genes (average±SEM). Clock genes tracked include Nr1d1 (-●-; filled circle), Arntl (-■-; filled square) Dbp (-▲-; filled triangle) Per2 (-▼-; filled inverted triangle) and Per1 (-♦-; filled diamond). (C) $PS_{50}$ values (average±SEM) of clock genes in the SCN (from B) and of activity reentrainment (from FIG. 1B). $P \leq 0.01$, *$P < 0.001$ versus Per2.

Because locomotor activity is believed to be driven by the circadian pacemaker of the SCN (Stephan and Zucker 1972; Sujino et al. 2003; Ralph et al. 1990; Sollars et al. 1995), adaptation to a new time zone should be reflected by changes of clock gene expression in the SCN. Hence, we used in situ hybridization (ISH) to determine jet lag-evoked changes in the transcription profiles of 5 canonical clock genes: Per1, Per2, Dbp, Nr1d1, and Arntl. Results of densitometric quantifications of autoradiographs of coronal sections through the SCN are depicted in FIG. 2A. Before the shift (day 0), transcripts of Per1, Per2, and Dbp showed rhythmic expression with peak levels around the middle of the day ($ZT_4$-$ZT_{10}$; FIG. 2A, top row). Arntl transcript levels were highest around $ZT_{16}$, while Nr1d1 mRNA levels peaked around the $ZT_0$ night/day transition. At 12 days after the shift, the transcript rhythms had fully adapted to the new LD cycle (FIG. 2A). Circadian transcript profiles of the different clock genes at intermediary time points showed marked differences in their individual adaptation characteristics.

To quantify the kinetics of adaptation of clock gene expression, we determined mRNA peaks by sine wave regression (FIG. 2A). The rhythmicity of circadian expression was verified using CircWave software (Oster et al. 2006). The time point of peak expression for each gene and day was determined. To facilitate a direct comparison of resetting of expression rhythms of different clock genes, peak times at days 2, 3, 4, and 12 were plotted relative to those at day 0 (FIG. 2B). Similar to our activity onset results (FIG. 1B), resetting of clock gene expression peaks followed sigmoid kinetics, with full reentrainment reached between day 3 (Per2) and day 8 (Nr1d1).

$PS_{50}$ values revealed a marked difference in adaptation kinetics among the different clock genes (FIG. 2C). Consistent with previous work (Yamazaki et al. 2000), period genes rapidly adapted to the new light schedule. Importantly, other clock genes showed a considerably slower rate of adaptation, more closely reflecting that seen for running-wheel activity (FIG. 2C).

Example 3

Peripheral Clocks Vary in their Rate of Adjustment During Jet Lag

Figure 3:
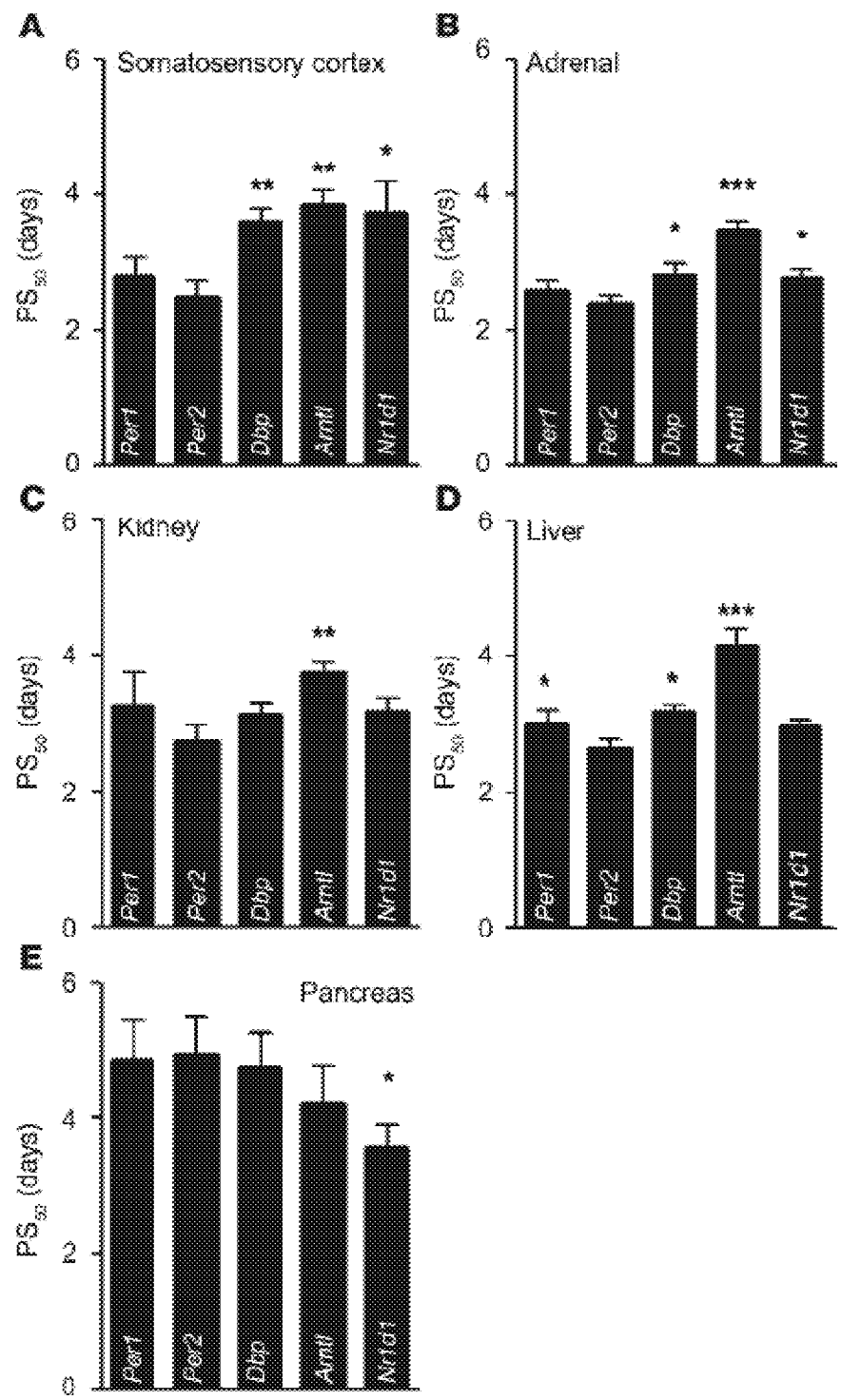
FIG. 3: Clock gene resetting kinetics in different tissues following 6-hour LD phase advance. Resetting is represented by $PS_{50}$ values (average±SEM). *$P \leq 0.05$, $P < 0.01$, *$P < 0.001$ versus Per2. Determination of $PS_{50}$ values from expression data (n=3 animals per time point) was done as described in FIG. 2. (A) In the somatosensory cortex, similar and rapid adaptation of the Per1 and Per2 was followed by slower adaptation of Dbp, Arntl, and Nr1d1. (B) In the adrenal, Per1 and Per2 both showed comparable and fast adaptation, whereas Dbp and Nr1d1 rhythms shifted at a similar, but slower, rate. Arntl showed the slowest adaptation, with a $PS_{50}$ value of 3.5±0.2 days. (C) A similar hierarchy was observed for kidney, with fast adaptation for Per, Dbp, and Nr1d1, and a slow one for Arntl. (D) In liver, Per2 expression shifted significantly faster than that of the other clock genes except Nr1d1. Per1 and Dbp followed at comparable speed, while Arntl adapted slowest (4.1±0.2 days). (E) In the pancreas, Per1 and Per2 shifting was slow, with PS50 values of 4.8±0.7 and 4.8±0.7 days, respectively, followed by Dbp and Arntl. Nr1d1 adaptation was fastest in this tissue, with a $PS_{50}$ value of 3.5±0.4 days.

In order to determine the rate of adaptation of peripheral clocks in mice subjected to jet lag conditions, we measured clock gene expression by quantitative real-time PCR (qPCR; adrenal, kidney, liver, and pancreas) or by ISH (somatosensory cortex) at days 0, 2, 3, 4, and 8 or 12 following a 6-hour advance of the LD cycle. Sine wave regression and F testing using CircWave software (Oster et al. 2006) showed that gene expression patterns were rhythmic at all times. PS50 values were determined as described above for the SCN; values for all tissues examined are shown in FIG. 3. Somatosensory cortex and SCN showed a similar pattern of clock gene adaptation (compare FIG. 2C and FIG. 3A). In both cases, we observed a rapid response of Per1 and Per2, followed by a slower response for Dbp, Arntl, and Nr1d1. The rate of adjustment of period genes was not as rapid in non-neuronal tissues, except for the adrenal. Per2 shifted fastest in kidney and liver, whereas Arntl shifted slowest and Per1 shifted slower, comparable to Dbp and Nr1d1 (FIG. 3, B-D). In stark contrast, Per1 and Per2 were both slow to reset in the pancreas, whereas Nr1d1 adjusted fast (FIG. 3E). Of note, $PS_{50}$ values in FIG. 3E were reconfirmed by repeated analysis yielding a P value of 0.05 or less for Nr1d1 versus Per2.

These data show that the order of clock gene resetting varied considerably among different organs, indicative of tissue-specific pathways of reentrainment. This misalignment in expression rhythms is thus a molecular hallmark of jet lag and a likely cause of its discomfort. Our data distinguish 3 different resetting groups: a CNS group, including the SCN and the somatosensory cortex, with fast responding period genes and slower, but comparably fast, readjustment of Dbp, Arntl, and Nr1d1; a group of peripheral tissues, such as the kidney and the liver, entraining via fast Per2, intermediate resetting of Per1, Dbp, and Nr1d1, and slow entrainment of Arntl; and the pancreas, showing an inversed order of clock gene resetting, with fast Nr1d1 and slow Per1, Per2, Dbp, and Arntl adaptation. The adrenal clock has an intermediate position between the first (CNS) and the peripheral reentrainment group, in agreement with its previously reported direct light entrainability (Oster et al. 2006; Ishida et al. 2005).

Our data thus indicate that the resetting mechanisms underlying the entrainment of peripheral clocks are highly tissue specific. In a similar paradigm in which animals were shifted from a long to a short photoperiod, differential resetting mechanisms were seen between the SCN and the liver (Sosniyenko et al. 2010). This study, as well as the present one, found that Per2 and Nr1d1 in the liver, but not in the SCN, shifted at comparably fast speeds. Such differential clock gene resetting lends further support to the hypothesis of differential and tissue-specific reentrainment. Interestingly, we found that the pancreas showed the slowest resetting kinetics of all tissue clocks analyzed in this study. This agrees with the finding that this organ has an exceptionally robust pacemaker (Muhlbauer et al. 2004; Peschke and Peschke 1998). Similar to the directly light-activated period genes in the SCN (Albrecht et al. 1997), fast shifting of Nr1d1 rhythms in the pancreas indicated that this gene might be an early target of resetting stimuli in this tissue. Several studies have characterized the nuclear orphan receptor Nr1d1 as a link between metabolic and circadian regulation (Raghuram et al. 2007; Yin et al. 2006; Meng et al. 2008; Ramakrishnan and Muscat 2006); hence, Nr1d1 may be a metabolic sensor setting the circadian clock in the pancreas.

Example 4

The Adrenal Clock Regulates Endocrine and Behavioral Reentrainment During Jet Lag Thus far, we showed that jet lag is characterized by a widespread, transient desynchronization of the molecular clockwork. However, it remains unclear by what mechanism the circadian system becomes realigned. Both the present study and recent work by others (Yamazaki et al. 2000; Reddy et al. 2002) showed that the SCN clock adapted fast to the new light schedule. Moreover, we found that such rapid reentrainment was also the case for the adrenal clock. It should be noted that adrenalectomized rats show an accelerated rate of reentrainment (Sage et al. 2004).

Figure 4:
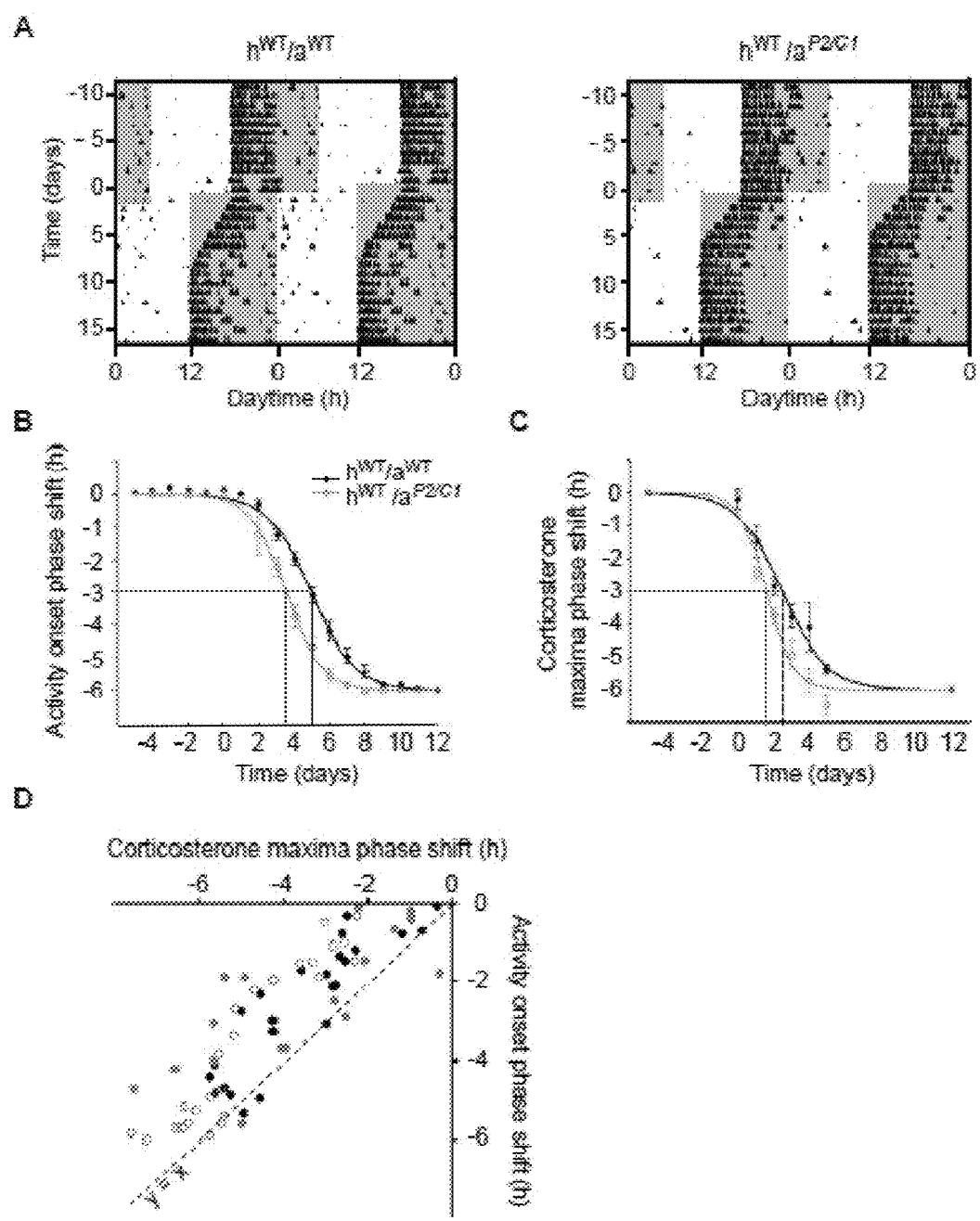
FIG. 4: Influence of adrenal clock function on activity reentrainment after 6-hour phase advance of the LD cycle. (A) Representative double-plot actograms of hWT/aWT and hWT/aP2/C1 animals. Dark phases are denoted by gray shading. (B) Resetting kinetics of activity onsets (average±SEM). The curves differed significantly between days 3 and 8 (0.003≤P≤0.016). On average, $PS_{50}$ values of activity resetting were reduced by 28.4% for hWT/aP2/C1. n=9 (hWT/aWT; closed circles, black trace); 8 (hWT/aP2/C1; open circles, lighter trace). (C) Resetting kinetics of corticosterone excretion maxima peak times (average±SEM). The curves differed significantly between days 2 and 5 (0.030≤P≤0.004). On average, $PS_{50}$ values of corticosterone resetting were reduced by 36.5% in hWT/aP2/C1. n=5 (hWT/aWT); 6 (hWT/aP2/C1). (D) Corticosterone maxima and activity onset phase shifts are plotted against each other for individual UT (closed gray circles), hWT/aWT (closed black circles), and hWT/aP2/C1 (open circles) mice. Because nearly all individual experimental values were located above the normal (y=x; dashed line), corticosterone concentration rhythms shifted more rapidly than did locomotor behavior at all times. A strong correlation between both factors for all groups was found (UT, r2=0.65; hWT/aWT, r2=0.79; hWT/aP2/C1, r2=0.87). UT activity is as shown in FIG. 1.

To examine whether the adrenal clock contributes to resynchronization, we analyzed the role of the adrenal circadian oscillator in our jet lag paradigm. First, we transplanted adrenals from clock-deficient Per2/Cry1 double-mutant animals into adrenalectomized WT hosts (Oster et al. 2006), creating adrenal clock-deficient mice (hostWT/ adrenalPer2/Cry1; referred to herein as hWT/aP2/C1). Animals were subjected to a 6-hour phase advance and the reentrainment of locomotor activity was compared with that of sham-operated controls (i.e., hWT/aWT). In the control group, wheel-running activity took approximately 9 days to fully adapt to the new LD cycle, whereas hWT/aP2/C1 mice adapted substantially faster, reaching full reentrainment around day 7 (FIGS. 4, A and B). PS50 values of activity onsets were 28.4% less in animals lacking an adrenal clock (hWT/aWT, 4.95±0.07 days; hWT/aP2/C1, 3.55±0.08 days; P<0.0001; F=161.4 [1, 266]).

The diurnal secretion rhythm of glucocorticoids from the adrenal is regulated by both SCN and adrenal circadian clocks (Oster et al. 2006; Son et al. 2008; Ishida et al. 2005). We therefore analyzed whether reentrainment kinetics of adrenal corticosterone rhythms parallel those of activity reentrainment in hWT/aP2/C1 animals. Fecal corticosterone excretion rhythms were measured at 4-hour intervals starting on day 0 and ending on day 5 relative to the phase shift. Additional samples were collected at days −5 and 12. Reentrainment kinetics was assessed by determining the shift of the sine-fitted peak time of corticosterone excretion. We found that the reentrainment of hormonal rhythms was significantly accelerated in mice lacking an adrenal clock (FIG. 4C). On average, the $PS_{50}$ values were reduced 36% in hWT/aP2/C1 animals (hWT/aWT, 2.47±0.17 days; hWT/aP2/C1, 1.57±0.10 days; P<0.0001; F=22.05 [1, 84]).

In both experimental groups, shifting of the glucocorticoid rhythm preceded shifting of activity (FIG. 4, compare B and C). This became particularly obvious by plotting locomotor activity onsets against hormonal peak time for transient days 1-5 for each of the 23 animals (FIG. 4D). This graph revealed a strong correlation between both parameters (hWT/aWT, r2=0.79; hWT/aP2/C1, r2=0.87). Almost all data points were located above the normal diagonal, reiterating that corticosterone concentration rhythms shift preceded that of locomotor behavior at all times. FIG. 4D also shows data points for untreated (UT; i.e., nonoperated) mice; even in this case, shifting of hormone rhythms preceded activity shifts (r2=0.65).

In summary, the lack of an adrenal circadian clock accelerated phase-shifting of an important endocrine factor (corticosterone) and of locomotor activity. Because the glucocorticoid phase shift preceded that of activity, this suggests that hormonal cues act as regulators of behavioral adaptation.

We and others have previously shown that the adrenal clock gates the response of the steroidogenic machinery to adrenocorticotropin and thereby influences the rhythm of glucocorticoid secretion into the blood (Oster et al. 2006; Son et al. 2008). Moreover, our behavioral data were indicative of a key regulatory function of the adrenal circadian clock in behavioral reentrainment during jet lag. Together with the role of glucocorticoids in the resetting of peripheral oscillators (Balsalobre et al. 2000), these findings suggest a critical role for the adrenal clock in the overall circadian entrainment process (Schibler et al. 2003; Le Minh et al. 2001). Both the SCN and the adrenal clock receive direct photic input through the autonomic nervous system (Oster et al. 2006; Ishida et al. 2005), which might account for the rapid entrainment response of these oscillators.

We posit that the SCN signals primarily though neuronal connections to the adrenal, thereby regulating adrenal clock gene expression. In turn, the adrenal clock feeds back to the SCN, where it stabilizes SCN-controlled activity rhythms. Glucocorticoids are part of this adrenal to SCN feedback, which most likely uses indirect pathway of transmission, as SCN neurons themselves do not express glucocorticoid receptors (Balsalobre et al. 2000; Rosenfeld et al. 1988). Such a feedback control mechanism would prevent uncoordinated resetting of the circadian system, for example in response to sporadic light exposure, and thus serves as a protection from Zeitgeber noise. In the case of jet lag, however, this feedback loop becomes a problem, preventing rapid adaptation of behavioral rhythms to the new time zone. When the adrenal clock is compromised, for example by adrenalectomy (Sage et al. 2004) or transplantation of a clock-deficient adrenal, then adrenal-SCN feedback is affected. The SCN pacemaker thus becomes less resistant to external perturbation and hence more rapidly relays the external resetting signal to subordinated clocks and tissues, resulting in accelerated reentrainment.

Example 5

Glucocorticoid Rhythms Regulate Reentrainment of Locomotor Activity

Figure 5:
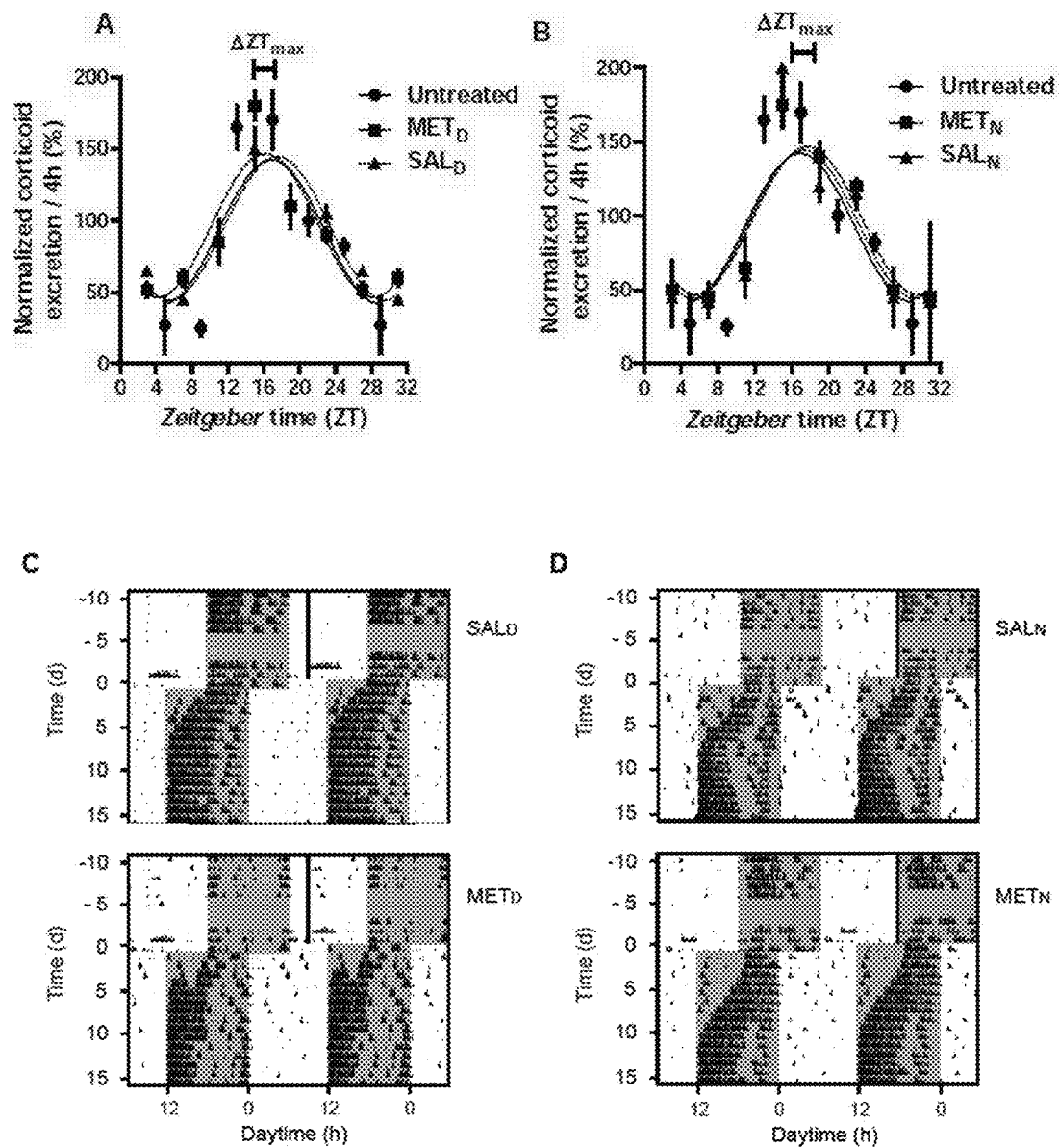
FIG. 5: Shifting corticosterone rhythms prior to jet lag affects behavioral resetting kinetics in a phase-advance paradigms. (A and B) Advanced and delayed corticosterone excretion rhythms of WT $MET_D$ (A) and $MET_N$ (B) mice after 16 days of metyrapone treatment. The direction of the shift of the corticosterone peak time prior to jet lag in treated mice in comparison to the peak time in $SAL_D$, $SAL_N$, and UT control mice (n=5) is indicated ($\Delta ZT_{max}$). (C and D) Representative double-plotted actograms of $SAL_D$ and $MET_D$ mice (C) and $SAL_N$ and $MET_N$ mice (D) 2 weeks before and 2 weeks after a 6-hour phase advance of the LD cycle. Time and duration of metyrapone treatment is shown by the dark vertical black bar. Dark phases are denoted by gray shading. (E and F) Resetting kinetics of activity onsets of $MET_D$ and $SAL_D$ mice (E), $MET_N$ and $SAL_N$ mice (F), and UT controls. Resetting kinetics of injected animals differed significantly from that of saline-treated animals (P<0.0001, MET$_D$ vs. SAL$_D$; P=0.0003, MET$_N$ vs. SAL$_N$; n=6 per group). All values are average±SEM. Untreated or UT (-●-); MET$_D$ and MET$_N$ (-■-); SAL$_D$ and SAL$_N$ (-▲-).
Figure 5:
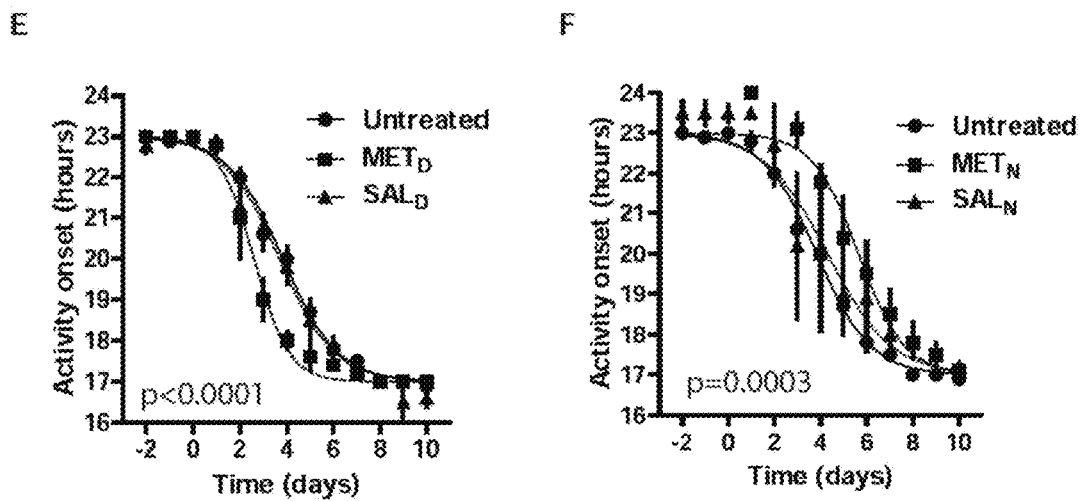

The possible role of adrenal glucocorticoids in mediating resynchronization offers an opportunity for experimental control of adjustment to jet lag. To manipulate endogenous glucocorticoid circadian profiles in mice, we injected metyrapone, which inhibits adrenal 11β-hydroxylase, an enzyme that converts 11-deoxycorticosterone to corticosterone. metyrapone was administered for 16 days at 2 different time points. One group of animals received daily i.p. injection of metyrapone during their inactive day phase, the other at the beginning of their active phase during the night (referred to herein as $MET_D$ and $MET_N$, respectively). Although this injection caused transient drowsiness, it had no effect on the onset of wheel-running activity of $MET_D$ mice, and only minor effect on the onset of $MET_N$ mice (FIGS. 5, C and D). UT and saline-injected animals (referred to herein as $SAL_D$ and $SAL_N$) were used as controls.

On the day prior to the phase shift (i.e., day 0), the corticosterone maximum in $MET_D$ mice was forward shifted by 1 hour relative to the $SAL_D$ control (from approximately $ZT_{17}$ to approximately $ZT_{16}$; FIG. 5A). Conversely, $MET_N$ mice showed peak corticosterone concentration at $ZT_{18}$, corresponding to a 1-hour backward shift relative to $SAL_N$ (FIG. 5B). Of note, metyrapone affected glucocorticoid peak times, but did not significantly change the amplitude of glucocorticoid excretion rhythms (data not shown). Sample actograms and activity onset plots emphasized that at the behavioral level, $MET_D$ mice showed accelerated activity resetting, whereas $MET_N$ animals reentrained slower (FIG. 5, C-F).

Figure 6:
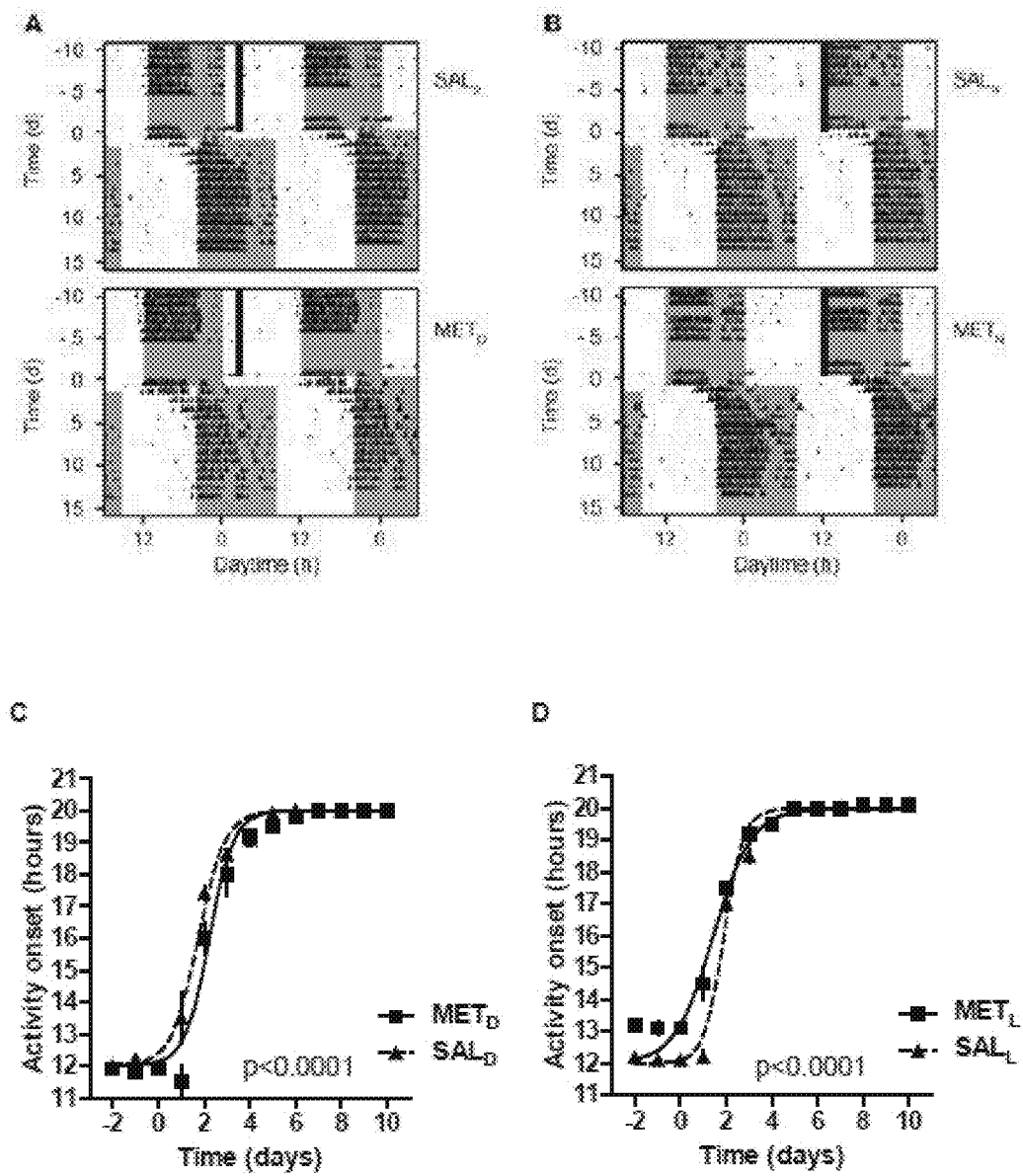
FIG. 6: Metyrapone injection prior to jet lag affects behavioral resetting kinetics in a phase-delay paradigm. After injection of metyrapone or saline for 16 days, animals were released into an 8-hour phase delay paradigm. (A and B) Representative double-plotted actograms of SAL$_D$ and MET$_D$ mice (A) and SAL$_N$ and MET$_N$ mice (B) 2 weeks before and 2 weeks after 8-hour phase delay of the LD cycle. Time and duration of metyrapone treatment is shown by the dark black bars. Dark phases are denoted by gray shading. (C and D) Resetting kinetics of activity onsets of MET$_D$ and SAL$_D$ mice (C) and MET$_N$ and SAL$_N$ mice (D). The curves of injected animals differed significantly from that of saline-treated control animals (P<0.0001, MET$_D$ vs. SAL$_D$ and MET$_N$ vs. SAL$_N$; n=6 per group). Differences between metyrapone- and saline-injected animals were still significant (P=0.0105) when the shift was shortened to 7 hours, caused by delayed onset after metyrapone injection at ZT$_{12}$. All values are average±SEM. MET$_D$ and MET$_N$ (-■-); SAL$_D$ and SAL$_N$ (-▲-).

To test whether metyrapone also influences resetting in a phase delay (westward traveling), we combined the above-described metyrapone injection studies with an 8-hour phase delay of the LD cycle. $MET_D$ and $MET_N$ animals shifted the rhythm of corticosterone secretion in a direction reminiscent of the phase-advance studies. After the LD shift, control mice entrained to the new LD cycle within 4-5 days (FIGS. 6, A and B). $MET_D$ mice showed decelerated adaptation, whereas $MET_N$ animals exhibited more rapid behavioural adaptation (FIGS. 6, C and D), indicating that the direction of the shift of the corticosterone peak time prior to jet lag determines the effect of metyrapone treatment on behavioral reentrainment.

Taken together, our data show that preconditioning mice by timed application of a glucocorticoid synthesis inhibitor influences the rate of behavioural resynchronization processes that follow a phase advance or delay. Although metyrapone treatment shifted the phase of glucocorticoid rhythms by only 1 or 2 hours, we observed a marked effect on photic reentrainment during jet lag. Thus our data underline the importance of glucocorticoid rhythms for photic adaptation. As an animal model of jet lag, the strategy of applying the 11β-hydroxylase inhibitor metyrapone to a normal animal seems more practical than adrenalectomy followed by imposing an endogenous glucocorticoid rhythm. To restore such rhythms requires implantation of slow-release pellets and restricted access to corticosterone-supplemented drinking water (Sage et al. 2004). Chronopharmacologic manipulation of glucocorticoid phase prior to jet lag by timed administration of metyrapone was sufficient to substantially accelerate or slow behavioral reentrainment and thus prolong or shorten the duration of jet lag. In another context, concurrent glucocorticoid administration and electrical stimulation was shown to promote hippocampal synaptic plasticity, whereas treatment with glucocorticoid prior to stimulation suppressed this effect (Wiegert et al. 2006; Alfarez et al. 2002; Pu et al. 2007). Both cases provide good examples for the clinical importance of timing in the design of therapeutic strategies.

In summary, our data show that in the SCN and in peripheral oscillators, the process of jet lag was characterized by marked heterogeneity of phase resetting of clock genes that operate in the positive and negative branches of the clock. The consequence is a transient misalignment of the transcriptional feedback loops driving the circadian molecular clock that results in deregulation of tissue-specific oscillators (Storch et al. 2002; Panda et al. 2002). Because circadian clocks control a large number of organotypic output genes, jet lag-associated desynchronisation of core clock genes across many organs will initiate a chain reaction culminating in transient perturbation of a wide range of physiological outputs. This perturbation alone would be sufficient to explain large aspects of the pathophysiology of the jet lag syndrome. Because glucocorticoid rhythmicity markedly influenced photic resetting during jet lag, modulating these rhythms by timed inhibition of glucocorticoid synthesis is considered an attractive therapeutic alternative because of its minor side effects. Since metyrapone is used in the diagnosis of adrenal insufficiency, its efficacy in alleviating jet lag can be investigated in humans.

In addition, the mouse model presented in our study may be used for screening for new chronopharmacologic agents to treat the various symptoms of jet lag affecting a large number of travelers and shift workers each day (Wittmann et al. 2006).

REFERENCES

Abe H, et al. Clock gene expressions in the suprachiasmatic nucleus and other areas of the brain during rhythm splitting in CS mice. *Brain Res Mol Brain Res.* 2001; 87(1):92-99.

Abraham D, Dallmann R, Steinlechner S, Albrecht U, Eichele G, Oster H. Restoration of circadian rhythmicity in circadian clock-deficient mice in constant light. *J Biol Rhythms.* 2006; 21(3):169-176.

Agostino P V, Plano S A, Golombek D A. Sildenafil accelerates reentrainment of circadian rhythms after advancing light schedules. *Proc Natl Acad Sci USA.* 2007; 104(23): 9834-9839.

Albrecht U, Sun Z S, Eichele G, Lee C. A differential response of two putative mammalian circadian regulators, mper1 and mper2, to light. *Cell.* 1997; 91(7):1055-1064.

Alfarez D N, Wiegert O, Joels M, Krugers H J. Corticosterone and stress reduce synaptic potentiation in mouse hippocampal slices with mild stimulation. NeuroScience. 2002; 115(4):1119-1126.

Arendt J. Managing jet lag: Some of the problems and possible new solutions. *Sleep Med. Rev.* 2009; 13(4):249-256.

Balsalobre A, et al. Resetting of circadian time in peripheral tissues by glucocorticoid signaling. *Science.* 2000; 289(5488):2344-2347.

Cho K, Ennaceur A, Cole J C, Suh C K. Chronic jet lag produces cognitive deficits. *J Neurosci.* 2000; 20(6):RC66.

Cho K. Chronic 'jet lag' produces temporal lobe atrophy and spatial cognitive deficits. *Nat. Neurosci.* 2001; 4(6):567-568.

Damiola F, Le Minh N, Preitner N, Kornmann B, Fleury-Olela F, Schibler U. Restricted feeding uncouples circadian oscillators in peripheral tissues from the central pacemaker in the suprachiasmatic nucleus. *Genes Dev.* 2000; 14(23): 2950-2961.

Davidson A J, Sellix M T, Daniel J, Yamazaki S, Menaker M, Block G D. Chronic jet-lag increases mortality in aged mice. *Curr Biol.* 2006; 16(21):R914-R916.

Davidson A J, Castanon-Cervantes O, Leise T L, Molyneux P C, Harrington M E. Visualizing jet lag in the mouse suprachiasmatic nucleus and peripheral circadian timing system. *Eur J. Neurosci.* 2009; 29(1):171-180.

Doghman M, Soltani Y, Rebuffet V, Naville D, Bégeot M. Role of Agouti-related protein in adrenal steroidogenesis. Mol Cell Endocrinol. 2007 February; 265-266:108-12.

Dunlap J C. Molecular bases for circadian clocks. *Cell.* 1999; 96(2):271-290.

Filipski E, et al. Effects of chronic jet lag on tumor progression in mice. Cancer Res. 2004; 64(21):7879-7885.

Haimov I, Arendt J. The prevention and treatment of jet lag. *Sleep Med. Rev.* 1999; 3(3):229-240.

Holder G. Measurement of glucocorticoids in biological fluids. Methods Mol. Biol. 2006; 324:141-57.

Ishida A, et al. Light activates the adrenal gland: timing of gene expression and glucocorticoid release. *Cell Metab.* 2005; 2(5):297-307.

Jakubcakova V, et al. Light entrainment of the mammalian circadian clock by a PRKCA-dependent posttranslational mechanism. *Neuron.* 2007; 54(5):831-843.

Jud C, Schmutz I, Hampp G, Oster H, Albrecht U. A guideline for analyzing circadian wheel-running behavior in rodents under different lighting conditions. *Biol Proced Online.* 2005; 7:101-116.

Kumar N, Solt L A, Wang Y, Rogers P M, Bhattacharyya G, Kamenecka T M, Stayrook K R, Crumbley C, Floyd Z E, Gimble J M, Griffin P R and Burri T P. Regulation of Adipogenesis by Natural and Synthetic REV-ERB Ligands. *Endocrinology* 2010; 151: 3015-3025.

Le Minh N, Damiola F, Tronche F, Schutz G, Schibler U. Glucocorticoid hormones inhibit foodinduced phase-shifting of peripheral circadian oscillators. *EMBO J.* 2001; 20(24):7128-7136.

Liu S, Cai Y, Sothern R B, Guan Y, Chan P. Chronobiological analysis of circadian patterns in transcription of seven key clock genes in six peripheral tissues in mice. *Chronobiol Int.* 2007; 24(5):793-820.

Meng Q J, et al. Ligand modulation of REVERBalpha function resets the peripheral circadian clock in a phasic manner. *J Cell Sci.* 2008; 121(pt 21):3629-3635.

Mohawk J A, Cashen K, Lee T M. Inhibiting cortisol response accelerates recovery from a photic phase shift. *Am J Physiol Regul Integr Comp Physiol.* 2005; 288(1):R221-R228.

Muhlbauer E, Wolgast S, Finckh U, Peschke D, Peschke E. Indication of circadian oscillations in the rat pancreas. *FEBS Lett.* 2004; 564(1-2):91-96.

Musholt T J, Klebs S H, Musholt P B, Ellerkamp V, Klempnauer J, Hoffmann M W. Transplantation of adrenal tissue fragments in a murine model: functional capacities of syngeneic and allogeneic grafts. *World J Surg.* 2002; 26(8): 950-957.

Müssig K, Remer T, Maser-Gluth C. J glucocorticoid excretion in obesity. Steroid Biochem Mol. Biol. 2010 August; 121(3-5):589-93.

Oishi K, Fukui H, Ishida N. Rhythmic expression of BMAL1 mRNA is altered in Clock mutant mice: differential regulation in the suprachiasmatic nucleus and peripheral tissues. *Biochem Biophys Res Commun.* 2000; 268(1):164-171.

Oster H, Yasui A, van der Horst G T, Albrecht U. Disruption of mCry2 restores circadian rhythmicity in mPer2 mutant mice. Genes Dev. 2002; 16(20):2633-2638.

Oster H, et al. The circadian rhythm of glucocorticoids is regulated by a gating mechanism residing in the adrenal cortical clock. *Cell Metab.* 2006; 4(2):163-173.

Oster H, Damerow S, Hut R A, Eichele G. Transcriptional profiling in the adrenal gland reveals circadian regulation of hormone biosynthesis genes and nucleosome assembly genes. *J Biol Rhythms.* 2006(a);21(5):350-361.

Panda S, et al. Coordinated transcription of key pathways in the mouse by the circadian clock. *Cell.* 2002; 109(3):307-320.

Penev P D, Kolker D E, Zee P C, Turek F W. Chronic circadian desynchronization decreases the survival of animals with cardiomyopathic heart disease. *Am J Physiol.* 1998; 275(6 pt 2):H2334-H2337.

Perreau-Lenz S, Pevet P, Buijs R M, Kalsbeek A. The biological clock: the bodyguard of temporal homeostasis. *Chronobiol Int.* 2004; 21(1):1-25.

Peschke E, Peschke D. Evidence for a circadian rhythm of insulin release from perifused rat pancreatic islets. *Diabetologia.* 1998; 41(9):1085-1092.

Preitner N, et al. The orphan nuclear receptor REVER-Balpha controls circadian transcription within the positive limb of the mammalian circadian oscillator. *Cell.* 2002; 110(2):251-260.

Pu Z, Krugers H J, Joels M. Corticosterone timedependently modulates beta-adrenergic effects on long-term potentiation in the hippocampal dentate gyms. Learn Mem. 2007; 14(5):359-367.

Raghuram S, et al. Identification of heme as the ligand for the orphan nuclear receptors REVERBalpha and REV-ERB-beta. *Nat Struct Mol. Biol.* 2007; 14(12):1207-1213.

Ralph M R, Foster R G, Davis F C, Menaker M. Transplanted suprachiasmatic nucleus determines circadian period. *Science.* 1990; 247(4945):975-978.

Ramakers C, Ruijter J M, Deprez R H, Moorman A F. Assumption-free analysis of quantitative real-time polymerase chain reaction (PCR) data. *Neurosci Lett.* 2003; 339(1):62-66.

Ramakrishnan S N, Muscat G E. The orphan Reverb nuclear receptors: a link between metabolism, circadian rhythm and inflammation? *Nucl Recept Signal.* 2006; 4:e009.

Reddy A B, Field M D, Maywood E S, Hastings M H. Differential resynchronisation of circadian clock gene expression within the suprachiasmatic nuclei of mice subjected to experimental jet lag. *J Neurosci.* 2002; 22(17):7326-7330.

Reddy T E, Pauli F, Sprouse R O, Neff N F, Newberry K M, Garabedian M J, Myers R M. Genomic determination of the glucocorticoid response reveals unexpected mechanisms of gene regulation. Genome Res. 2009 December; 19(12):2163-71.

Reppert S M, Weaver D R. Molecular analysis of mammalian circadian rhythms. *Annu Rev Physiol.* 2001; 63:647-676.

Ripperger J A, Shearman L P, Reppert S M, Schibler U. CLOCK, an essential pacemaker component, controls expression of the circadian transcription factor DBP. *Genes Dev.* 2000; 14(6):679-689.

Rosenfeld P, Van Eekelen J A, Levine S, De Kloet E R. Ontogeny of the type 2 glucocorticoid receptor in discrete rat brain regions: an immunocytochemical study. *Brain Res.* 1988; 470(1):119-127.

Sage D, et al. Influence of the corticosterone rhythm on photic entrainment of locomotor activity in rats. *J Biol Rhythms.* 2004; 19(2):144-156.

Schibler U, Ripperger J, Brown S A. Peripheral circadian oscillators in mammals: time and food. *J Biol Rhythms.* 2003; 18(3):250-260.

Sollars P J, Kimble D P, Pickard G E. Restoration of circadian behavior by anterior hypothalamic heterografts. *J. Neurosci.* 1995; 15(3 pt 2):2109-2122.

Son G H, et al. Adrenal peripheral clock controls the autonomous circadian rhythm of glucocorticoid by causing rhythmic steroid production. *Proc Natl Acad Sci USA.* 2008; 105(52):20970-20975.

Sosniyenko S, Parkanova D, Illnerova H, Sladek M, Sumova A. Different mechanisms of adjustment to a change of the photoperiod in the suprachiasmatic and liver circadian clocks. *Am J Physiol Regul Integr Comp Physiol.* 2010; 298(4):R959-R971.

Srinivasan V, Spence D W, Pandi-Perumal S R, Trakht I, Cardinali D P. Jet lag: therapeutic use of melatonin and possible application of melatonin analogs. *Travel Med Infect Dis.* 2008; 6(1-2):17-28.

Stephan F K, Zucker I. Circadian rhythms in drinking behavior and locomotor activity of rats are eliminated by hypothalamic lesions. *Proc Natl Acad Sci USA.* 1972; 69(6):1583-1586.

Stocco, D. M., Wang, X., Jo, Y., and Manna, P. R. (2005). Multiple signalling pathways regulating steroidogenesis and steroidogenic acute regulatory protein expression: more complicated than we thought. Mol. Endocrinol. 19, 2647-2659.

Storch K F, et al. Extensive and divergent circadian gene expression in liver and heart. *Nature.* 2002; 417(6884):78-83.

Sujino M, Masumoto K H, Yamaguchi S, van der Horst G T, Okamura H, Inouye S T. Suprachiasmatic nucleus grafts restore circadian behavioural rhythms of genetically arrhythmic mice. *Curr Biol.* 2003; 13(8):664-668.

Tapp W N, Natelson B H. Circadian rhythms and patterns of performance before and after simulated jet lag. *Am J Physiol.* 1989; 257(4 pt 2):R796-R803.

Tosini G, Menaker M. Circadian rhythms in cultured mammalian retina. *Science.* 1996; 272(5260):419-421.

Ulrich-Lai Y M, Engeland W C. Rat adrenal transplants are reinnervated: an invalid model of denervated adrenal cortical tissue. *J. Neuroendocrinol.* 2000; 12(9):881-893.

van der Horst G T, et al. Mammalian Cry1 and Cry2 are essential for maintenance of circadian rhythms. *Nature.* 1999; 398(6728):627-630.

Waterhouse J, Reilly T, Atkinson G, Edwards B. Jet lag: trends and coping strategies. *Lancet.* 2007; 369(9567):1117-1129.

Welsh D K, Yoo S H, Liu A C, Takahashi J S, Kay S A. Bioluminescence imaging of individual fibroblasts reveals persistent, independently phased circadian rhythms of clock gene expression. *Curr Biol.* 2004; 14(24):2289-2295.

Wiegert O, Joels M, Krugers H. Timing is essential for rapid effects of corticosterone on synaptic potentiation in the mouse hippocampus. Learn Mem. 2006; 13(2):110-113.

Wittmann M, Dinich J, Merrow M, Roenneberg T. Social jetlag: misalignment of biological and social time. *Chronobiol Int.* 2006; 23(1-2):497-509.

Yamazaki S, et al. Resetting central and peripheral circadian oscillators in transgenic rats. *Science*. 2000; 288(5466): 682-685.

Yan L, Miyake S, Okamura H. Distribution and circadian expression of dbp in SCN and extra-SCN areas in the mouse brain. *J Neurosci Res*. 2000; 59(2):291-295.

Yin L, Wang J, Klein P S, Lazar M A. Nuclear receptor Rev-erbalpha is a critical lithium-sensitive component of the circadian clock. *Science*. 2006; 311(5763):1002-1005.

Yoo S H, et al. PERIOD2:LUCIFERASE real-time reporting of circadian dynamics reveals persistent circadian oscillations in mouse peripheral tissues. *Proc Natl Acad Sci US A*. 2004; 101(15):5339-5346.

What is claimed is:

1. A method of preventing or treating symptoms and/or diseases associated with jet lag comprising administering to a subject in need thereof a pharmaceutically effective amount of a modulator of glucocorticoid biosynthesis, wherein the modulator inhibits the conversion of 11-deoxycortisol to cortisol and is selected from FAD286, metyrapone, etomidate, or FAD.

2. The method of claim 1, wherein the modulator is a modulator of Cyp11b1.

3. The method of claim 1, wherein the symptoms and/or diseases associated with jet lag are selected from the group consisting of sleep disruption, impaired cognitive skills, loss of appetite, depression, reduced psychomotor coordination, gastrointestinal disturbances, decreased alertness, malignant cell growth, temporal lobe atrophy, and cardiomyopathies.

4. The method of claim 3, wherein the amplitude of maximum amounts of glucocorticoids is not significantly altered.

5. The method of claim 3, wherein the time point of maximum amounts of glucocorticoids in a subject treated with said modulator is earlier than the time point of maximum amounts of glucocorticoids from a subject not treated with the modulator and wherein this earlier time point results from the administration of the modulator in the first half of the rest phase of the subject to be treated.

6. The method of claim 3, wherein the time point of maximum amounts of glucocorticoids in a subject treated with the modulator is later than the time point of maximum amounts of glucocorticoids from a subject not treated with the modulator and wherein this later time point results from the administration of the modulator in the first half of the active phase of the subject to be treated.

7. The method of claim 1, wherein the modulator is administered at least one time prior to and/or at the time of initiating activities that cause jet lag.

8. The method of claim 7, wherein the modulator is administered once a day.

9. The method of claim 2, wherein the modulator is a small organic molecule.

* * * * *